(12) United States Patent
Funamura et al.

(10) Patent No.: US 8,939,938 B2
(45) Date of Patent: Jan. 27, 2015

(54) NEEDLE TIP PROTECTOR

(75) Inventors: Shigeaki Funamura, Shizuoka-ken (JP);
Yoshihiro Wada, Shizuoka-ken (JP);
Yosuke Sakai, Shizuoka-ken (JP)

(73) Assignee: Covidien LP, Mansfield, MA (US)

( * ) Notice: Subject to any disclaimer, the term of this patent is extended or adjusted under 35 U.S.C. 154(b) by 733 days.

(21) Appl. No.: 12/445,413

(22) PCT Filed: Oct. 12, 2007

(86) PCT No.: PCT/US2007/021794
§ 371 (c)(1),
(2), (4) Date: Jan. 18, 2010

(87) PCT Pub. No.: WO2008/045530
PCT Pub. Date: Apr. 17, 2008

(65) Prior Publication Data
US 2010/0137803 A1    Jun. 3, 2010

(30) Foreign Application Priority Data
Oct. 12, 2006    (JP) .................. 2006-278436

(51) Int. Cl.
*A61M 5/178* (2006.01)
*A61M 25/06* (2006.01)
*A61M 5/32* (2006.01)

(52) U.S. Cl.
CPC ......... *A61M 25/0618* (2013.01); *A61M 5/3273* (2013.01)
USPC .................................................. 604/164.08

(58) Field of Classification Search
USPC ............... 604/164.08, 167.01, 246, 248, 256, 604/167.06
See application file for complete search history.

(56) References Cited

U.S. PATENT DOCUMENTS

| | | | |
|---|---|---|---|
| 1,502,278 A * | 7/1924 | Stevens | 449/27 |
| 3,134,380 A | 5/1964 | Armao | |
| 3,884,230 A | 5/1975 | Wulff | |
| 4,387,879 A | 6/1983 | Tauschinski | |
| 4,512,766 A | 4/1985 | Vailancourt | |

(Continued)

FOREIGN PATENT DOCUMENTS

| | | |
|---|---|---|
| EP | 2 119 468 | 11/2009 |
| JP | 09099069 A | 4/1997 |

(Continued)

OTHER PUBLICATIONS

PCT International Search Report for International Application No. PCT/US2007/021794 dated Apr. 24, 2008 (7 pgs.).

(Continued)

*Primary Examiner* — Manuel Mendez
(74) *Attorney, Agent, or Firm* — John Paul Mello, Esq.

(57) ABSTRACT

The present disclosure is directed to an indwelling needle set which includes a needle tip protector device which adds a minimal length to the needle set to maintain operability of the device. To accomplish this, a needle tip protector device is provided for releasable attachment to the needle set. The protector device includes a body and a protecting sleeve which is movable through an opening in the body from an advanced position located substantially within the body to a retracted position extending rearwardly from the body. The protecting sleeve is dimensioned to slidably receive a puncturing needle which includes an increased diameter position which cannot be withdrawn through the protecting sleeve.

24 Claims, 10 Drawing Sheets

(56) References Cited

U.S. PATENT DOCUMENTS

| | | |
|---|---|---|
| 4,725,267 A | 2/1988 | Vaillancourt |
| 4,755,170 A | 7/1988 | Golden |
| 4,778,453 A | 10/1988 | Lopez |
| 4,795,432 A | 1/1989 | Karczmer |
| 4,804,370 A | 2/1989 | Haber |
| 4,804,371 A | 2/1989 | Vaillancourt |
| 4,808,169 A | 2/1989 | Haber |
| 4,834,718 A | 5/1989 | Mc donald |
| 4,842,591 A | 6/1989 | Luther |
| 4,846,805 A | 7/1989 | Sitar |
| 4,850,977 A | 7/1989 | Bayless |
| 4,850,994 A | 7/1989 | Zerbst |
| 4,863,434 A | 9/1989 | Bayless |
| 4,863,436 A | 9/1989 | Glick |
| 4,867,746 A | 9/1989 | Dufresne |
| 4,874,377 A | 10/1989 | Newgard |
| 4,908,022 A | 3/1990 | Haber |
| 4,909,794 A | 3/1990 | Haber |
| 4,911,706 A | 3/1990 | Levitt |
| 4,917,668 A | 4/1990 | Haindl |
| 4,921,486 A | 5/1990 | De chellis |
| 4,921,490 A | 5/1990 | Spier |
| 4,927,415 A | 5/1990 | Brodsky |
| 4,929,241 A | 5/1990 | Kulli |
| 4,931,040 A | 6/1990 | Haber |
| 4,935,010 A | 6/1990 | Cox |
| 4,944,723 A | 7/1990 | Haber |
| 4,944,728 A | 7/1990 | Carrell |
| 4,952,207 A | 8/1990 | Lemieux |
| 4,955,866 A | 9/1990 | Corey |
| 4,964,854 A | 10/1990 | Luther |
| 4,978,343 A | 12/1990 | Dysarz |
| 4,978,344 A | 12/1990 | Dombrowski |
| 4,986,813 A | 1/1991 | Blake, III |
| 4,986,819 A | 1/1991 | Sobel |
| 4,994,041 A | 2/1991 | Dombrowski |
| 4,994,046 A | 2/1991 | Wesson |
| 4,998,922 A | 3/1991 | Kuracina |
| 5,002,533 A | 3/1991 | Jullien |
| 5,013,305 A | 5/1991 | Opie |
| 5,015,234 A | 5/1991 | Jullien |
| 5,015,240 A | 5/1991 | Soproni |
| 5,015,241 A | 5/1991 | Feimer |
| 5,015,242 A | 5/1991 | Heifetz |
| 5,030,208 A | 7/1991 | Novacek |
| 5,049,136 A | 9/1991 | Johnson |
| 5,051,109 A | 9/1991 | Simon |
| 5,053,014 A | 10/1991 | Van heugten |
| 5,053,017 A | 10/1991 | Chamuel |
| 5,059,180 A | 10/1991 | Mclees |
| 5,059,184 A | 10/1991 | Dyke |
| 5,080,651 A | 1/1992 | Julien |
| 5,084,018 A | 1/1992 | Tsao |
| 5,085,648 A | 2/1992 | Purdy |
| 5,092,461 A | 3/1992 | Adam |
| 5,092,851 A | 3/1992 | Ragner |
| 5,104,378 A | 4/1992 | Haber |
| 5,112,311 A | 5/1992 | Utterberg |
| 5,114,404 A | 5/1992 | Paxton |
| 5,120,321 A | 6/1992 | Oksman |
| 5,122,118 A | 6/1992 | Haber |
| 5,122,124 A | 6/1992 | Novacek |
| 5,127,905 A | 7/1992 | Lemieux |
| 5,131,405 A | 7/1992 | Burns |
| 5,135,504 A | 8/1992 | Mc lees |
| 5,137,515 A | 8/1992 | Hogan |
| 5,147,327 A | 9/1992 | Johnson |
| 5,154,699 A | 10/1992 | Ryan |
| 5,154,703 A | 10/1992 | Bonaldo |
| 5,156,596 A | 10/1992 | Balbierz |
| 5,158,554 A | 10/1992 | Jepson |
| 5,169,391 A | 12/1992 | Vogel |
| 5,171,229 A | 12/1992 | Mc neil |
| 5,171,300 A | 12/1992 | Blake, III |
| 5,176,650 A | 1/1993 | Haining |
| 5,176,655 A | 1/1993 | Mc cormick |
| 5,176,656 A | 1/1993 | Bayless |
| 5,180,369 A | 1/1993 | Dysarz |
| 5,180,370 A | 1/1993 | Gillespie |
| 5,183,468 A | 2/1993 | Mclees |
| 5,188,607 A | 2/1993 | Wu |
| 5,195,723 A | 3/1993 | Schauerte |
| 5,195,974 A | 3/1993 | Hardy |
| 5,195,980 A | 3/1993 | Catlin |
| 5,199,947 A | 4/1993 | Lopez |
| 5,205,827 A | 4/1993 | Novacek |
| 5,205,829 A | 4/1993 | Lituchy |
| 5,207,656 A | 5/1993 | Kranys |
| 5,211,629 A | 5/1993 | Pressly |
| 5,211,633 A | 5/1993 | Stouder, Jr. |
| 5,215,525 A | 6/1993 | Sturman |
| 5,215,528 A | 6/1993 | Purdy |
| 5,215,533 A | 6/1993 | Robb |
| 5,215,534 A | 6/1993 | De harde |
| 5,215,538 A | 6/1993 | Larkin |
| 5,222,505 A | 6/1993 | Burns |
| 5,224,936 A | 7/1993 | Gallagher |
| 5,228,646 A | 7/1993 | Raines |
| 5,232,456 A | 8/1993 | Gonzalez |
| 5,232,458 A | 8/1993 | Chen |
| 5,234,410 A | 8/1993 | Graham |
| 5,242,393 A | 9/1993 | Brimball |
| 5,242,400 A | 9/1993 | Blake, III |
| 5,242,402 A | 9/1993 | Chen |
| 5,242,411 A | 9/1993 | Yamamoto |
| 5,246,427 A | 9/1993 | Sturman |
| RE34,416 E | 10/1993 | Lemieux |
| 5,251,873 A | 10/1993 | Atkinson |
| 5,254,099 A | 10/1993 | Kuracina |
| 5,256,152 A | 10/1993 | Marks |
| 5,261,880 A | 11/1993 | Streck |
| 5,261,894 A | 11/1993 | Smith |
| 5,263,933 A | 11/1993 | Novacek |
| 5,266,072 A | 11/1993 | Utterberg |
| 5,267,966 A | 12/1993 | Paul |
| 5,267,976 A | 12/1993 | Guerineau |
| 5,269,763 A | 12/1993 | Boehmer |
| 5,269,764 A | 12/1993 | Vetter |
| 5,269,765 A | 12/1993 | Kuracina |
| 5,269,771 A | 12/1993 | Thomas |
| 5,273,540 A | 12/1993 | Luther |
| 5,277,342 A | 1/1994 | Dickau |
| 5,279,570 A | 1/1994 | Dombrowski |
| 5,279,571 A | 1/1994 | Larkin |
| 5,279,591 A | 1/1994 | Simon |
| 5,290,246 A | 3/1994 | Yamamoto |
| 5,293,970 A | 3/1994 | Schneider |
| 5,295,657 A | 3/1994 | Atkinson |
| 5,295,658 A | 3/1994 | Atkinson |
| 5,295,963 A | 3/1994 | Deeks |
| 5,295,972 A | 3/1994 | Mischenko |
| 5,297,777 A | 3/1994 | Yie |
| 5,300,032 A | 4/1994 | Hibbs |
| 5,300,033 A | 4/1994 | Miller |
| 5,300,034 A | 4/1994 | Behnke |
| 5,300,035 A | 4/1994 | Clement |
| 5,300,040 A | 4/1994 | Martin |
| 5,300,045 A | 4/1994 | Plassche, Jr. |
| 5,304,136 A | 4/1994 | Erskine |
| 5,304,151 A | 4/1994 | Kuracina |
| 5,304,156 A | 4/1994 | Sylvanowicz |
| 5,306,243 A | 4/1994 | Bonaldo |
| 5,308,336 A | 5/1994 | Hart |
| 5,312,355 A | 5/1994 | Lee |
| 5,312,362 A | 5/1994 | Pfolsgraf |
| 5,312,363 A | 5/1994 | Ryan |
| 5,312,371 A | 5/1994 | Dombrowski |
| 5,312,372 A | 5/1994 | De harde |
| 5,322,517 A | 6/1994 | Sircom |
| 5,322,518 A | 6/1994 | Schneider |
| 5,324,271 A | 6/1994 | Abiuso |
| 5,328,478 A | 7/1994 | Mcvay |
| 5,328,482 A | 7/1994 | Sircom |
| 5,328,484 A | 7/1994 | Somers |

(56) References Cited

U.S. PATENT DOCUMENTS

| | | |
|---|---|---|
| 5,328,485 A | 7/1994 | Moreno |
| 5,330,435 A | 7/1994 | Vaillancourt |
| 5,330,437 A | 7/1994 | Durman |
| 5,334,158 A | 8/1994 | Mc lees |
| 5,334,159 A | 8/1994 | Turkel |
| 5,336,192 A | 8/1994 | Palestrant |
| 5,336,198 A | 8/1994 | Silver |
| 5,336,199 A | 8/1994 | Castillo |
| 5,336,200 A | 8/1994 | Streck |
| 5,342,316 A | 8/1994 | Wallace |
| 5,342,319 A | 8/1994 | Watson |
| 5,344,161 A | 9/1994 | Sandgren |
| 5,344,408 A | 9/1994 | Partika |
| 5,344,414 A | 9/1994 | Lopez |
| 5,348,544 A | 9/1994 | Sweeney |
| 5,350,362 A | 9/1994 | Stouder, Jr. |
| 5,350,363 A | 9/1994 | Goode |
| 5,352,205 A | 10/1994 | Dales |
| 5,353,837 A | 10/1994 | Faust |
| 5,354,280 A | 10/1994 | Haber |
| 5,356,384 A | 10/1994 | Haber |
| 5,360,413 A | 11/1994 | Leason |
| 5,364,370 A | 11/1994 | Szerlip |
| 5,364,372 A | 11/1994 | Danks |
| 5,368,574 A | 11/1994 | Antonacci |
| 5,376,077 A | 12/1994 | Gomringer |
| 5,380,288 A | 1/1995 | Hart |
| 5,380,305 A | 1/1995 | Ghouri |
| 5,382,235 A | 1/1995 | Sak |
| 5,383,860 A | 1/1995 | Lau |
| 5,385,550 A | 1/1995 | Su |
| 5,389,081 A | 2/1995 | Castro |
| 5,390,898 A | 2/1995 | Smedley |
| 5,395,338 A | 3/1995 | Gaba |
| 5,395,346 A | 3/1995 | Maggioni |
| 5,395,347 A | 3/1995 | Blecher |
| 5,395,352 A | 3/1995 | Penny |
| 5,403,284 A | 4/1995 | Gross |
| 5,405,323 A | 4/1995 | Rogers |
| 5,405,327 A | 4/1995 | Chen |
| 5,405,331 A | 4/1995 | Behnke |
| 5,409,461 A | 4/1995 | Steinman |
| 5,409,464 A | 4/1995 | Villalobos |
| 5,411,486 A | 5/1995 | Zadini |
| 5,411,492 A | 5/1995 | Sturman |
| 5,415,638 A | 5/1995 | Novacek |
| 5,417,659 A | 5/1995 | Gaba |
| 5,417,673 A | 5/1995 | Gordon |
| 5,419,766 A | 5/1995 | Chang |
| 5,423,766 A | 6/1995 | Cesare |
| 5,425,718 A | 6/1995 | Tay |
| 5,425,720 A | 6/1995 | Rogalsky |
| 5,429,596 A | 7/1995 | Arias |
| 5,429,619 A | 7/1995 | Furnish |
| 5,431,631 A | 7/1995 | Lu |
| 5,431,632 A | 7/1995 | Lu |
| 5,433,703 A | 7/1995 | Utterberg |
| 5,437,646 A | 8/1995 | Hunt |
| 5,439,451 A | 8/1995 | Collinson |
| 5,441,487 A | 8/1995 | Vedder |
| 5,443,452 A | 8/1995 | Hart |
| 5,443,454 A | 8/1995 | Tanabe |
| 5,447,501 A | 9/1995 | Karlsson |
| 5,453,095 A | 9/1995 | Davila |
| 5,454,790 A | 10/1995 | Dubrul |
| 5,456,284 A | 10/1995 | Ryan |
| 5,456,675 A | 10/1995 | Wolbring |
| 5,458,640 A | 10/1995 | Gerrone |
| 5,458,658 A | 10/1995 | Sircom |
| 5,460,603 A | 10/1995 | Desantis |
| 5,462,531 A | 10/1995 | Novacek |
| 5,465,938 A | 11/1995 | Werge |
| 5,466,223 A | 11/1995 | Bressler |
| 5,466,230 A | 11/1995 | Davila |
| 5,470,319 A | 11/1995 | Mayer |
| 5,472,418 A | 12/1995 | Palestrant |
| 5,474,544 A | 12/1995 | Lynn |
| 5,478,313 A | 12/1995 | White |
| 5,480,393 A | 1/1996 | Bommarito |
| 5,484,401 A | 1/1996 | Rodriguez |
| 5,486,190 A | 1/1996 | Green |
| 5,487,728 A | 1/1996 | Vaillancourt |
| 5,487,733 A | 1/1996 | Caizza |
| 5,487,850 A | 1/1996 | Vanderploeg |
| 5,489,274 A | 2/1996 | Chu |
| 5,492,147 A | 2/1996 | Challender |
| 5,492,304 A | 2/1996 | Smith |
| 5,496,274 A | 3/1996 | Graves |
| 5,496,280 A | 3/1996 | Vandenbroek |
| 5,501,426 A | 3/1996 | Atkinson |
| 5,501,670 A | 3/1996 | Sak |
| 5,501,675 A | 3/1996 | Erskine |
| 5,507,732 A | 4/1996 | Mcclure |
| 5,509,433 A | 4/1996 | Paradis |
| 5,514,098 A | 5/1996 | Pfolsgraf |
| 5,514,116 A | 5/1996 | Vaillancourt |
| 5,514,117 A | 5/1996 | Lynn |
| 5,520,649 A | 5/1996 | Novacek |
| 5,520,655 A | 5/1996 | Davila |
| 5,520,666 A | 5/1996 | Choudhury |
| 5,531,701 A | 7/1996 | Luther |
| 5,533,974 A | 7/1996 | Gaba |
| 5,533,975 A | 7/1996 | Lu |
| 5,535,785 A | 7/1996 | Werge |
| 5,538,505 A | 7/1996 | Weinstein |
| 5,538,508 A | 7/1996 | Steyn |
| 5,540,661 A | 7/1996 | Tomisaka |
| 5,540,662 A | 7/1996 | Nicholson |
| 5,545,146 A | 8/1996 | Ishak |
| 5,545,152 A | 8/1996 | Funderburk |
| 5,549,565 A | 8/1996 | Ryan |
| 5,549,566 A | 8/1996 | Elias |
| 5,549,570 A | 8/1996 | Rogalsky |
| 5,549,576 A | 8/1996 | Patterson |
| 5,549,651 A | 8/1996 | Lynn |
| 5,554,131 A | 9/1996 | Lacivita |
| 5,558,651 A | 9/1996 | Crawford |
| 5,562,629 A | 10/1996 | Haughton |
| 5,562,630 A | 10/1996 | Nichols |
| 5,562,632 A | 10/1996 | Davila |
| 5,562,633 A | 10/1996 | Wozencroft |
| 5,562,636 A | 10/1996 | Utterberg |
| 5,562,637 A | 10/1996 | Utterberg |
| 5,569,202 A | 10/1996 | Kovalic |
| 5,569,203 A | 10/1996 | Chen |
| 5,569,205 A | 10/1996 | Hart |
| 5,569,209 A | 10/1996 | Roitman |
| 5,569,288 A | 10/1996 | Yoon |
| 5,573,545 A | 11/1996 | Yoon |
| 5,575,774 A | 11/1996 | Chen |
| 5,575,777 A | 11/1996 | Cover et al. |
| 5,575,804 A | 11/1996 | Yoon |
| 5,578,059 A | 11/1996 | Patzer |
| 5,582,594 A | 12/1996 | Chen |
| 5,582,597 A | 12/1996 | Brimhall |
| 5,584,808 A | 12/1996 | Healy |
| 5,584,809 A | 12/1996 | Gaba |
| 5,584,810 A | 12/1996 | Brimhall |
| 5,584,818 A | 12/1996 | Morrison |
| 5,584,848 A | 12/1996 | Yoon |
| 5,584,849 A | 12/1996 | Yoon |
| 5,584,850 A | 12/1996 | Hart |
| 5,588,966 A | 12/1996 | Atsumi |
| 5,591,134 A | 1/1997 | Shu |
| 5,591,137 A | 1/1997 | Stevens |
| 5,591,190 A | 1/1997 | Yoon |
| 5,591,193 A | 1/1997 | Yoon |
| 5,599,310 A | 2/1997 | Bogert |
| 5,601,532 A | 2/1997 | Gaba |
| 5,601,534 A | 2/1997 | Turner |
| 5,601,536 A | 2/1997 | Crawford |
| 5,607,396 A | 3/1997 | Yoon |
| 5,607,439 A | 3/1997 | Yoon |
| 5,611,781 A | 3/1997 | Sircom |

(56) References Cited

U.S. PATENT DOCUMENTS

| | | |
|---|---|---|
| 5,611,792 A | 3/1997 | Gustafsson |
| 5,613,500 A | 3/1997 | Bishop |
| 5,613,663 A | 3/1997 | Schmidt |
| 5,613,952 A | 3/1997 | Pressly, Sr. |
| 5,613,954 A | 3/1997 | Nelson |
| 5,613,956 A | 3/1997 | Patterson |
| 5,616,129 A | 4/1997 | Mayer |
| 5,616,130 A | 4/1997 | Mayer |
| 5,618,271 A | 4/1997 | Yoon |
| 5,630,803 A | 5/1997 | Tamaro |
| 5,634,913 A | 6/1997 | Stinger |
| 5,634,934 A | 6/1997 | Yoon |
| 5,643,227 A | 7/1997 | Stevens |
| 5,645,076 A | 7/1997 | Yoon |
| 5,645,533 A | 7/1997 | Blaeser |
| 5,651,772 A | 7/1997 | Arnett |
| 5,653,698 A | 8/1997 | Niedospial |
| 5,662,610 A | 9/1997 | Sircom |
| 5,669,891 A | 9/1997 | Vaillancourt |
| 5,672,160 A | 9/1997 | Osterlind |
| 5,672,161 A | 9/1997 | Allen |
| 5,676,681 A | 10/1997 | Yoon |
| 5,676,682 A | 10/1997 | Yoon |
| 5,676,683 A | 10/1997 | Yoon |
| 5,683,365 A | 11/1997 | Brown |
| 5,683,368 A | 11/1997 | Schmidt |
| 5,685,855 A | 11/1997 | Erskine |
| 5,685,860 A | 11/1997 | Chang |
| 5,688,240 A | 11/1997 | Novacek |
| 5,688,253 A | 11/1997 | Paradis |
| 5,688,254 A | 11/1997 | Lopez |
| 5,688,286 A | 11/1997 | Yoon |
| 5,693,025 A | 12/1997 | Stevens |
| 5,693,031 A | 12/1997 | Ryan |
| 5,695,474 A | 12/1997 | Daugherty |
| 5,696,466 A | 12/1997 | Li |
| 5,697,907 A | 12/1997 | Gaba |
| 5,699,821 A | 12/1997 | Paradis |
| 5,700,249 A | 12/1997 | Jenkins |
| 5,700,250 A | 12/1997 | Erskine |
| 5,702,367 A | 12/1997 | Cover |
| 5,709,664 A | 1/1998 | Vandenbroek |
| 5,718,688 A | 2/1998 | Wozencroft |
| 5,718,689 A | 2/1998 | Stevenson |
| 5,718,691 A | 2/1998 | Russo |
| 5,720,734 A | 2/1998 | Copenhaver |
| 5,722,958 A | 3/1998 | Gravener |
| 5,725,503 A | 3/1998 | Arnett |
| 5,735,827 A | 4/1998 | Adwers |
| 5,738,144 A | 4/1998 | Rogers |
| 5,738,665 A | 4/1998 | Caizza |
| 5,743,884 A | 4/1998 | Hasson |
| 5,743,888 A | 4/1998 | Wilkes |
| 5,743,891 A | 4/1998 | Tolkoff et al. |
| 5,746,718 A | 5/1998 | Steyn |
| 5,749,857 A | 5/1998 | Cuppy |
| 5,749,859 A | 5/1998 | Powell |
| 5,749,861 A | 5/1998 | Guala |
| 5,749,889 A | 5/1998 | Bacich |
| 5,755,699 A | 5/1998 | Blecher |
| 5,755,701 A | 5/1998 | Sarstedt |
| 5,772,636 A | 6/1998 | Brimhall |
| 5,776,113 A | 7/1998 | Daugherty |
| 5,779,681 A | 7/1998 | Bonn |
| 5,779,684 A | 7/1998 | Tamaro |
| 5,782,804 A | 7/1998 | Mcmahon |
| D397,434 S | 8/1998 | Pike |
| 5,788,676 A | 8/1998 | Yoon |
| 5,792,121 A | 8/1998 | Tamaro |
| 5,795,339 A | 8/1998 | Erskine |
| 5,797,897 A | 8/1998 | Jepson |
| 5,800,403 A | 9/1998 | Pressly, Sr. |
| 5,803,919 A | 9/1998 | Hart |
| 5,806,831 A | 9/1998 | Paradis |
| 5,807,350 A | 9/1998 | Diaz |
| 5,807,352 A | 9/1998 | Tamaro |
| 5,807,353 A | 9/1998 | Schmitz |
| 5,810,784 A | 9/1998 | Tamaro |
| 5,814,018 A | 9/1998 | Elson |
| 5,817,069 A | 10/1998 | Arnett |
| 5,817,070 A | 10/1998 | Tamaro |
| 5,820,606 A | 10/1998 | Davis |
| 5,820,614 A | 10/1998 | Erskine |
| 5,820,621 A | 10/1998 | Yale |
| 5,830,189 A | 11/1998 | Chang |
| 5,833,670 A | 11/1998 | Dillon |
| 5,851,196 A | 12/1998 | Arnett |
| 5,853,393 A | 12/1998 | Bogert |
| 5,853,399 A | 12/1998 | Sasaki |
| 5,857,999 A | 1/1999 | Quick |
| 5,858,000 A | 1/1999 | Novacek |
| 5,858,007 A | 1/1999 | Fagan |
| 5,865,806 A | 2/1999 | Howell |
| 5,871,471 A | 2/1999 | Ryan |
| 5,879,331 A | 3/1999 | Osterlind |
| 5,879,337 A | 3/1999 | Kuracina |
| 5,882,337 A | 3/1999 | Bogert |
| 5,885,256 A | 3/1999 | Chern et al. |
| 5,891,093 A | 4/1999 | Dysarz |
| 5,899,887 A | 5/1999 | Liu |
| 5,910,130 A | 6/1999 | Caizza |
| 5,911,705 A | 6/1999 | Howell |
| 5,911,710 A | 6/1999 | Barry |
| 5,916,198 A | 6/1999 | Dillow |
| 5,919,168 A | 7/1999 | Wheeler |
| 5,919,174 A | 7/1999 | Hanson |
| 5,925,020 A | 7/1999 | Nestell |
| 5,935,104 A | 8/1999 | Janek |
| 5,941,850 A | 8/1999 | Shah |
| 5,951,515 A | 9/1999 | Osterlind |
| 5,951,529 A | 9/1999 | Utterberg |
| 5,954,698 A | 9/1999 | Pike |
| 5,954,708 A | 9/1999 | Lopez |
| 5,957,887 A | 9/1999 | Osterlind |
| 5,957,898 A | 9/1999 | Jepson |
| 5,967,490 A | 10/1999 | Pike |
| 5,968,068 A | 10/1999 | Dehdashtian |
| 5,971,957 A | 10/1999 | Luther |
| 5,989,224 A | 11/1999 | Exline |
| 5,993,419 A | 11/1999 | Lo |
| 5,997,486 A | 12/1999 | Burek |
| 5,997,507 A | 12/1999 | Dysarz |
| 6,001,080 A | 12/1999 | Kuracina |
| 6,004,294 A | 12/1999 | Brimhall |
| 6,012,213 A | 1/2000 | Chang |
| 6,015,397 A | 1/2000 | Elson |
| 6,024,729 A | 2/2000 | Dehdashtian |
| 6,033,386 A | 3/2000 | Novacek |
| 6,036,672 A | 3/2000 | Allen |
| 6,039,302 A | 3/2000 | Cote, Sr. |
| 6,048,335 A | 4/2000 | Mayer |
| 6,053,861 A | 4/2000 | Grossi |
| 6,068,011 A | 5/2000 | Paradis |
| 6,074,370 A | 6/2000 | Pressly, Jr. |
| 6,077,244 A | 6/2000 | Botich |
| 6,079,432 A | 6/2000 | Paradis |
| 6,080,135 A | 6/2000 | Van Stokkum |
| 6,080,137 A | 6/2000 | Pike |
| 6,086,566 A | 7/2000 | Arnissolle |
| 6,090,074 A * | 7/2000 | Brimhall et al. .......... 604/167.05 |
| 6,099,500 A | 8/2000 | Dysarz |
| 6,099,505 A | 8/2000 | Ryan |
| 6,102,894 A | 8/2000 | Dysarz |
| RE36,885 E | 9/2000 | Blecher |
| 6,117,107 A | 9/2000 | Chen |
| 6,117,108 A | 9/2000 | Woehr |
| 6,117,110 A | 9/2000 | Radmand |
| 6,117,113 A | 9/2000 | Novacek |
| 6,127,320 A | 10/2000 | Ooij et al. |
| 6,152,900 A | 11/2000 | Mayer |
| 6,156,010 A | 12/2000 | Kuracina |
| 6,159,185 A | 12/2000 | Tanihata |
| 6,162,196 A | 12/2000 | Hart |
| 6,171,287 B1 | 1/2001 | Lynn |

(56) References Cited

U.S. PATENT DOCUMENTS

| | | |
|---|---|---|
| 6,183,440 B1 | 2/2001 | Bell |
| 6,183,448 B1 | 2/2001 | Mayer |
| 6,193,690 B1 | 2/2001 | Dysarz |
| 6,200,262 B1 | 3/2001 | Ouchi |
| 6,203,527 B1 | 3/2001 | Zadini |
| 6,203,533 B1 | 3/2001 | Ouchi |
| 6,206,857 B1 | 3/2001 | Chen |
| 6,210,373 B1 | 4/2001 | Allmon |
| 6,213,978 B1 | 4/2001 | Voyten |
| 6,217,555 B1 | 4/2001 | Hart |
| 6,217,568 B1 | 4/2001 | Jepson |
| 6,221,047 B1 | 4/2001 | Greene |
| 6,221,050 B1 | 4/2001 | Ishida |
| 6,221,056 B1 | 4/2001 | Silverman |
| 6,224,569 B1 | 5/2001 | Brimhall |
| 6,228,060 B1 | 5/2001 | Howell |
| 6,234,999 B1 | 5/2001 | Wemmert |
| 6,235,003 B1 | 5/2001 | Dysarz |
| 6,235,006 B1 | 5/2001 | Dillon |
| 6,241,707 B1 | 6/2001 | Dysarz |
| 6,245,045 B1 | 6/2001 | Stratienko |
| 6,245,048 B1 | 6/2001 | Fangrow |
| 6,254,529 B1 | 7/2001 | Ouchi |
| 6,258,065 B1 | 7/2001 | Dennis |
| 6,261,264 B1 | 7/2001 | Tamaro |
| 6,261,265 B1 | 7/2001 | Mosseri |
| 6,273,869 B1 | 8/2001 | Vaillancourt |
| 6,277,100 B1 | 8/2001 | Raulerson |
| 6,280,419 B1 | 8/2001 | Vojtasek |
| 6,287,278 B1 | 9/2001 | Woehr |
| 6,287,279 B1 | 9/2001 | Siekmann |
| 6,287,280 B1 | 9/2001 | Lampropoulos |
| 6,306,124 B1 | 10/2001 | Jones |
| 6,322,537 B1 | 11/2001 | Chang |
| 6,322,541 B2 | 11/2001 | West |
| 6,342,045 B1 | 1/2002 | Somers |
| 6,344,031 B1 | 2/2002 | Novacek |
| 6,344,033 B1 | 2/2002 | Jepson |
| 6,352,520 B1 | 3/2002 | Miyazaki |
| 6,352,521 B1 | 3/2002 | Prosl |
| 6,358,265 B1 | 3/2002 | Thorne, Jr. |
| 6,379,332 B1 | 4/2002 | Van Landuyt |
| 6,379,333 B1 | 4/2002 | Brimhall |
| 6,379,372 B1 | 4/2002 | Dehdashtian |
| 6,394,983 B1 | 5/2002 | Mayoral |
| 6,402,721 B1 | 6/2002 | Lo |
| 6,406,459 B1 | 6/2002 | Allmon |
| 6,409,703 B1 | 6/2002 | Lu |
| 6,413,236 B1 | 7/2002 | Van Dyke |
| 6,416,499 B2 | 7/2002 | Paul, Jr. |
| 6,425,884 B1 | 7/2002 | Wemmert |
| 6,440,101 B1 | 8/2002 | Grabenkort |
| 6,443,927 B1 | 9/2002 | Cook |
| 6,443,929 B1 | 9/2002 | Kuracina |
| 6,461,328 B2 | 10/2002 | Wang |
| 6,475,194 B2 | 11/2002 | Domici, Jr. |
| 6,485,459 B1 | 11/2002 | Surowitz |
| 6,485,468 B2 | 11/2002 | Vojtasek |
| 6,488,656 B1 | 12/2002 | Wu |
| 6,488,663 B1 | 12/2002 | Steg |
| 6,488,674 B2 | 12/2002 | Becker |
| 6,506,181 B2 | 1/2003 | Meng |
| 6,520,939 B2 | 2/2003 | Lafontaine |
| 6,524,276 B1 | 2/2003 | Halseth |
| 6,524,278 B1 | 2/2003 | Campbell |
| 6,527,747 B2 | 3/2003 | Adams |
| 6,530,903 B2 | 3/2003 | Wang |
| 6,533,759 B1 | 3/2003 | Watson |
| 6,537,259 B1 | 3/2003 | Niermann |
| 6,545,242 B1 | 4/2003 | Butler |
| 6,551,283 B1 | 4/2003 | Guo |
| 6,569,119 B1 | 5/2003 | Haberland |
| 6,572,591 B2 | 6/2003 | Mayer |
| 6,582,402 B1 | 6/2003 | Erskine |
| 6,585,701 B1 | 7/2003 | Dysarz |
| 6,585,704 B2 | 7/2003 | Luther |
| 6,592,555 B1 | 7/2003 | Wen-Pi et al. |
| 6,592,556 B1 | 7/2003 | Thorne |
| 6,595,954 B1 | 7/2003 | Luther |
| 6,595,955 B2 | 7/2003 | Ferguson |
| 6,595,964 B2 | 7/2003 | Finley |
| 6,595,965 B1 | 7/2003 | Utterberg |
| 6,595,981 B2 | 7/2003 | Huet |
| 6,602,240 B2 | 8/2003 | Hermann |
| 6,605,073 B1 | 8/2003 | Pressly, Sr. |
| 6,610,031 B1 | 8/2003 | Chin |
| 6,616,630 B1 | 9/2003 | Woehr |
| 6,616,640 B2 | 9/2003 | Chen |
| 6,620,136 B1 | 9/2003 | Pressly, Sr. |
| 6,623,458 B2 | 9/2003 | Woehr |
| 6,629,959 B2 | 10/2003 | Kuracina |
| 6,632,200 B2 | 10/2003 | Potter et al. |
| 6,632,201 B1 | 10/2003 | Mathias |
| 6,641,564 B1 | 11/2003 | Kraus |
| 6,651,956 B2 | 11/2003 | Miller |
| 6,652,486 B2 | 11/2003 | Bialecki |
| 6,652,490 B2 | 11/2003 | Howell |
| 6,663,592 B2 | 12/2003 | Rhad |
| 6,663,599 B2 | 12/2003 | Osborne |
| 6,669,666 B2 | 12/2003 | Lu |
| 6,669,681 B2 | 12/2003 | Dudar et al. |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fanegrow, Jr. |
| 6,699,221 B2 | 3/2004 | Vaillancourt |
| 6,706,022 B1 | 3/2004 | Leinsing |
| 6,709,419 B2 | 3/2004 | Woehr |
| 6,712,791 B2 | 3/2004 | Lui |
| 6,719,726 B2 | 4/2004 | Meng |
| 6,723,073 B2 | 4/2004 | Ley |
| 6,736,798 B2 | 5/2004 | Ohkubo |
| 6,743,199 B2 | 6/2004 | Shue |
| 6,749,588 B1 | 6/2004 | Howell |
| 6,761,704 B2 | 7/2004 | Crawford |
| 6,761,705 B1 | 7/2004 | Chiu |
| 6,761,706 B2 | 7/2004 | Vaillancourt |
| 6,764,468 B1 | 7/2004 | East |
| 6,767,340 B2 | 7/2004 | Willis |
| 6,770,059 B1 | 8/2004 | Spinks |
| 6,773,416 B1 | 8/2004 | Hsu |
| 6,776,774 B2 | 8/2004 | Tansey, Jr. |
| 6,796,962 B2 | 9/2004 | Ferguson |
| 6,796,968 B2 | 9/2004 | Ferguson |
| 6,796,969 B1 | 9/2004 | Andersson |
| 6,802,827 B2 | 10/2004 | Andersson |
| 6,808,161 B1 | 10/2004 | Hishikawa |
| 6,808,509 B1 | 10/2004 | Davey |
| 6,811,545 B2 | 11/2004 | Vaillancourt |
| 6,817,989 B2 | 11/2004 | Svendsen |
| 6,821,266 B2 | 11/2004 | Knepshield |
| 6,824,527 B2 | 11/2004 | Gollobin |
| 6,832,992 B2 | 12/2004 | Wilkinson |
| 6,855,127 B2 | 2/2005 | Nakagami |
| 6,855,130 B2 | 2/2005 | Saulenas |
| 6,860,869 B2 | 3/2005 | Dennis |
| 6,860,871 B2 | 3/2005 | Kuracina |
| 6,863,659 B2 | 3/2005 | Sharpe |
| 6,866,656 B2 | 3/2005 | Tingey |
| 6,878,131 B2 | 4/2005 | Novacek |
| 6,878,134 B2 | 4/2005 | Rogers |
| 6,883,778 B1 | 4/2005 | Newton |
| 6,884,224 B2 | 4/2005 | Dalton |
| 6,886,808 B2 | 5/2005 | Sarno |
| 6,893,423 B2 | 5/2005 | Denolly |
| 6,902,546 B2 | 6/2005 | Ferguson |
| 6,905,483 B2 | 6/2005 | Newby |
| 6,908,459 B2 | 6/2005 | Harding |
| 6,911,018 B2 | 6/2005 | Gordon |
| 6,913,595 B2 | 7/2005 | Mastorakis |
| 6,916,309 B2 | 7/2005 | Fangrow, Jr. |
| 6,916,311 B2 | 7/2005 | Vojtasek |
| 6,918,891 B2 | 7/2005 | Bressler |

(56) References Cited

U.S. PATENT DOCUMENTS

| | | |
|---|---|---|
| 6,921,382 B2 | 7/2005 | Lee |
| 6,921,386 B2 | 7/2005 | Shue |
| 6,926,698 B2 | 8/2005 | Lin |
| 6,926,700 B2 | 8/2005 | Bressler |
| 6,929,622 B2 | 8/2005 | Chian |
| 6,932,803 B2 | 8/2005 | Newby |
| 6,936,031 B2 | 8/2005 | Caleffi |
| 6,936,036 B2 | 8/2005 | Wilkinson |
| 6,942,642 B2 | 9/2005 | Suzuki |
| 6,958,055 B2 | 10/2005 | Donnan |
| 6,972,002 B2 | 12/2005 | Thorne |
| 6,979,314 B2 | 12/2005 | Hsieh |
| 6,981,965 B2 | 1/2006 | Luther |
| 6,984,213 B2 | 1/2006 | Horner |
| 6,986,759 B1 | 1/2006 | Jeremijevic |
| 6,991,215 B2 | 1/2006 | Kiehne |
| RE38,996 E | 2/2006 | Crawford |
| 6,997,902 B2 | 2/2006 | Thorne |
| 7,004,927 B2 | 2/2006 | Ferguson |
| 7,004,934 B2 | 2/2006 | Vaillancourt |
| 7,008,402 B2 | 3/2006 | Ferguson |
| 7,008,404 B2 * | 3/2006 | Nakajima ............ 604/158 |
| 7,014,623 B2 | 3/2006 | Prestidge |
| 7,018,344 B2 | 3/2006 | Bressler |
| 7,018,365 B2 | 3/2006 | Strauss |
| 7,025,721 B2 | 4/2006 | Cohen |
| 7,025,744 B2 | 4/2006 | Utterberg |
| 7,033,339 B1 | 4/2006 | Lynn |
| 7,033,345 B2 | 4/2006 | Lee |
| 7,037,292 B2 | 5/2006 | Carlyon |
| 7,037,303 B2 | 5/2006 | Beaufore |
| 7,060,053 B2 | 6/2006 | Nakashima |
| 7,063,685 B2 | 6/2006 | Rome |
| 7,066,908 B2 | 6/2006 | Kuracina |
| 7,077,824 B2 | 7/2006 | Meyer |
| 7,081,106 B1 | 7/2006 | Guo |
| 7,083,596 B2 | 8/2006 | Saied |
| 7,083,600 B2 | 8/2006 | Meloul |
| 7,101,351 B2 | 9/2006 | Crawford |
| 7,101,353 B2 | 9/2006 | Lui |
| 7,104,970 B2 | 9/2006 | Chen |
| 7,112,191 B2 | 9/2006 | Daga |
| 7,125,396 B2 | 10/2006 | Leinsing |
| 7,125,397 B2 | 10/2006 | Woehr |
| 7,147,621 B2 | 12/2006 | Kiehne |
| 7,150,725 B2 | 12/2006 | Wilkinson |
| 7,160,269 B2 | 1/2007 | Woehr |
| 7,172,580 B2 | 2/2007 | Hruska |
| 7,175,610 B2 | 2/2007 | Mori |
| 7,179,244 B2 | 2/2007 | Smith |
| 7,182,734 B2 | 2/2007 | Saulenas |
| 7,186,239 B2 | 3/2007 | Woehr |
| 7,192,433 B2 | 3/2007 | Osypka |
| 7,198,618 B2 | 4/2007 | Ferguson |
| 7,207,975 B2 | 4/2007 | Miller |
| 7,214,208 B2 | 5/2007 | Vaillancourt |
| 7,214,211 B2 | 5/2007 | Woehr |
| 7,226,434 B2 | 6/2007 | Carlyon |
| 7,235,062 B2 | 6/2007 | Brustad |
| 7,238,169 B2 | 7/2007 | Takagi |
| 7,239,169 B2 | 7/2007 | Isa |
| 7,247,148 B2 | 7/2007 | Murashita |
| 7,252,651 B2 | 8/2007 | Haider |
| 7,264,613 B2 | 9/2007 | Woehr |
| 7,291,128 B2 | 11/2007 | Rossi |
| 7,291,130 B2 | 11/2007 | McGurk |
| 7,297,138 B2 | 11/2007 | Fangrow, Jr. |
| 7,300,419 B2 | 11/2007 | Fangrow, Jr. |
| 7,303,548 B2 | 12/2007 | Rhad |
| 7,306,579 B2 | 12/2007 | Fujii |
| 7,309,326 B2 | 12/2007 | Fangrow, Jr. |
| 7,311,693 B2 | 12/2007 | Shekalim |
| 7,311,694 B2 | 12/2007 | Fangrow, Jr. |
| 7,314,462 B2 | 1/2008 | O'Reagan |
| 7,314,463 B2 | 1/2008 | Fangrow, Jr. |
| 7,316,667 B2 | 1/2008 | Lindstrom |
| 7,318,818 B2 | 1/2008 | Yashiro |
| 7,326,189 B2 | 2/2008 | Mori |
| 7,331,934 B2 | 2/2008 | Suresh |
| 7,331,935 B2 | 2/2008 | Barere |
| 7,331,939 B2 | 2/2008 | Fangrow, Jr. |
| 7,341,573 B2 | 3/2008 | Ferguson |
| 7,347,838 B2 | 3/2008 | Kulli |
| 7,347,839 B2 | 3/2008 | Hiejima |
| 7,347,842 B2 | 3/2008 | Thorne |
| 7,354,422 B2 | 4/2008 | Riesenberger |
| 7,357,784 B2 | 4/2008 | Ferguson |
| 7,361,164 B2 | 4/2008 | Simpson |
| 7,371,226 B2 | 5/2008 | Huang |
| 7,371,227 B2 | 5/2008 | Zeiner |
| 7,374,554 B2 | 5/2008 | Menzi |
| 7,387,616 B2 | 6/2008 | Li |
| 7,396,346 B2 | 7/2008 | Nakajima |
| 7,399,293 B2 | 7/2008 | Oyibo |
| 7,407,491 B2 | 8/2008 | Fangrow, Jr. |
| 7,407,495 B2 | 8/2008 | Barere |
| 7,413,562 B2 | 8/2008 | Ferguson |
| 7,422,571 B2 | 9/2008 | Schweikert |
| 7,422,573 B2 | 9/2008 | Wilkinson |
| 7,445,611 B2 | 11/2008 | Osborne |
| 7,458,954 B2 | 12/2008 | Ferguson |
| 7,470,254 B2 | 12/2008 | Basta |
| 7,470,261 B2 | 12/2008 | Lynn |
| 7,470,262 B2 | 12/2008 | Hiejima |
| 7,497,847 B2 | 3/2009 | Crawford |
| 7,497,849 B2 | 3/2009 | Fangrow, Jr. |
| 7,500,965 B2 | 3/2009 | Menzi |
| 7,507,222 B2 | 3/2009 | Cindrich |
| 7,513,887 B2 | 4/2009 | Halseth |
| 7,513,888 B2 | 4/2009 | Sircom et al. |
| 7,524,300 B2 | 4/2009 | Patton |
| 7,530,965 B2 | 5/2009 | Villa |
| 7,534,227 B2 | 5/2009 | Kulli |
| 7,534,231 B2 | 5/2009 | Kuracina |
| 7,537,582 B2 | 5/2009 | Suresh |
| 7,544,181 B2 | 6/2009 | Axelsson |
| 7,566,323 B2 | 7/2009 | Chang |
| 7,566,327 B2 | 7/2009 | Mathias |
| 7,569,033 B2 | 8/2009 | Greene |
| 7,572,247 B2 | 8/2009 | Smith |
| 7,575,570 B2 | 8/2009 | Barere |
| 7,578,803 B2 | 8/2009 | Rome |
| 7,578,805 B2 | 8/2009 | Hwang |
| 7,578,806 B2 | 8/2009 | Zeoli |
| 7,591,449 B2 | 9/2009 | Raines |
| 7,597,681 B2 | 10/2009 | Sutton |
| 7,597,684 B2 | 10/2009 | Alchas |
| 7,601,139 B2 | 10/2009 | Woehr |
| 7,604,616 B2 | 10/2009 | Thoresen |
| 7,608,057 B2 | 10/2009 | Woehr |
| 7,611,485 B2 | 11/2009 | Ferguson |
| 7,611,487 B2 | 11/2009 | Woehr |
| 7,611,488 B2 | 11/2009 | Chang |
| 7,611,499 B2 | 11/2009 | Woehr |
| 7,614,423 B2 | 11/2009 | Yokota |
| 7,618,395 B2 | 11/2009 | Ferguson |
| 7,625,360 B2 | 12/2009 | Woehr |
| 7,628,774 B2 | 12/2009 | Fangrow, Jr. |
| 7,628,776 B2 | 12/2009 | Gibson |
| 7,632,243 B2 | 12/2009 | Bialecki |
| 7,635,352 B2 | 12/2009 | Adams |
| 7,635,357 B2 | 12/2009 | Mayer |
| 7,637,887 B2 | 12/2009 | Woehr |
| 7,637,888 B2 | 12/2009 | Schwarzbich |
| 7,637,893 B2 | 12/2009 | Christensen |
| 7,651,476 B2 | 1/2010 | Kohler |
| 7,651,481 B2 | 1/2010 | Raybuck |
| 7,654,988 B2 | 2/2010 | Moulton |
| 7,658,725 B2 | 2/2010 | Bialecki |
| 7,662,134 B2 | 2/2010 | Miller |
| 7,666,170 B2 | 2/2010 | Guala |
| 7,670,317 B2 | 3/2010 | Cindrich |
| 7,670,320 B2 | 3/2010 | Iwase |
| 7,682,331 B2 | 3/2010 | Carrez |

(56) References Cited

U.S. PATENT DOCUMENTS

| | | |
|---|---|---|
| 7,682,339 B2 | 3/2010 | Fujii |
| 7,682,340 B2 | 3/2010 | Funamura |
| 7,686,784 B2 | 3/2010 | Baik |
| 7,691,088 B2 | 4/2010 | Howell |
| 7,694,403 B2 | 4/2010 | Moulton |
| 7,713,242 B2 | 5/2010 | Streifinger |
| 7,713,243 B2 | 5/2010 | Hillman |
| 7,713,250 B2 | 5/2010 | Harding |
| 7,713,256 B2 | 5/2010 | Brimhall |
| 7,713,257 B2 | 5/2010 | Brimhall |
| 7,717,888 B2 | 5/2010 | Vaillancourt |
| 7,722,563 B2 | 5/2010 | Isaacson |
| 7,722,564 B2 | 5/2010 | Vaillancourt |
| 7,722,569 B2 | 5/2010 | Soderholm et al. |
| 7,727,198 B2 | 6/2010 | Nakajima |
| 7,731,687 B2 | 6/2010 | Menzi |
| 7,731,694 B2 | 6/2010 | Becker |
| 7,736,332 B2 | 6/2010 | Carlyon |
| 7,736,337 B2 | 6/2010 | Diep |
| 7,736,339 B2 | 6/2010 | Woehr |
| 7,736,340 B2 | 6/2010 | Harding |
| 7,736,342 B2 | 6/2010 | Abriles |
| 7,740,613 B2 | 6/2010 | Yokoi |
| 7,740,614 B2 | 6/2010 | Murashita |
| 7,744,567 B2 | 6/2010 | Glowacki et al. |
| 7,744,568 B2 | 6/2010 | Douglas |
| 7,744,570 B2 | 6/2010 | Fangrow, Jr. |
| 7,753,338 B2 | 7/2010 | Desecki |
| 7,753,877 B2 | 7/2010 | Bialecki |
| 7,753,887 B2 | 7/2010 | Botich |
| 7,758,543 B2 | 7/2010 | Ferraresi |
| 7,762,986 B2 | 7/2010 | Wang |
| 7,763,199 B2 | 7/2010 | Fangrow, Jr. |
| 7,771,412 B2 | 8/2010 | Anderson |
| 7,785,296 B2 | 8/2010 | Muskatello |
| 7,794,445 B2 | 9/2010 | Dalton |
| 7,794,675 B2 | 9/2010 | Lynn |
| 7,798,994 B2 | 9/2010 | Brimhall |
| 7,806,849 B2 | 10/2010 | Woehr |
| 7,806,858 B2 | 10/2010 | Smith |
| 7,806,869 B2 | 10/2010 | Nilsson |
| 7,806,890 B2 | 10/2010 | McKinnon |
| 7,811,261 B2 | 10/2010 | Rubinstein |
| 7,815,614 B2 | 10/2010 | Fangrow, Jr. |
| 7,824,393 B2 | 11/2010 | Fangrow |
| 7,828,773 B2 | 11/2010 | Swisher |
| 7,828,774 B2 | 11/2010 | Harding |
| 7,833,199 B2 | 11/2010 | Franer |
| 7,850,648 B2 | 12/2010 | Gratwohl |
| 7,850,650 B2 | 12/2010 | Breitweiser |
| 7,850,652 B2 | 12/2010 | Liniger |
| 7,867,204 B2 | 1/2011 | Bartholomew |
| 7,887,516 B2 | 2/2011 | Young |
| 7,892,209 B2 | 2/2011 | Harand |
| 7,892,216 B2 | 2/2011 | Fangrow, Jr. |
| 7,901,379 B2 | 3/2011 | Argentine |
| 7,905,857 B2 | 3/2011 | Swisher |
| 7,914,488 B2 | 3/2011 | Dickerson |
| 7,914,494 B2 | 3/2011 | Hiejima |
| 7,914,519 B2 | 3/2011 | Moran |
| 7,922,698 B2 | 4/2011 | Riesenberger |
| 7,927,314 B2 | 4/2011 | Kuracina |
| 7,931,615 B2 | 4/2011 | Fangrow, Jr. |
| 7,931,622 B2 | 4/2011 | Beling |
| 7,935,080 B2 | 5/2011 | Howell |
| 7,935,090 B2 | 5/2011 | Patton |
| 7,938,805 B2 | 5/2011 | Harding |
| 7,947,018 B2 | 5/2011 | Mckinnon |
| 7,947,032 B2 | 5/2011 | Harding |
| 7,951,119 B2 | 5/2011 | Leeflang |
| 7,951,122 B2 | 5/2011 | Shekalim |
| 7,955,306 B2 | 6/2011 | Wyss |
| 7,959,613 B2 | 6/2011 | Rhad |
| 7,967,797 B2 | 6/2011 | Winsor |
| 7,972,300 B2 | 7/2011 | Smith |
| 7,972,313 B2 | 7/2011 | Woehr |
| 7,976,498 B2 | 7/2011 | Swisher |
| 7,976,502 B2 | 7/2011 | Baid |
| 7,976,503 B2 | 7/2011 | Khan |
| 7,981,090 B2 | 7/2011 | Plishka |
| 7,985,199 B2 | 7/2011 | Kornerup |
| 7,985,232 B2 | 7/2011 | Potter |
| 7,988,664 B2 | 8/2011 | Fiser |
| 7,993,305 B2 | 8/2011 | Ye |
| 7,993,306 B2 | 8/2011 | Marrs |
| 7,998,122 B2 | 8/2011 | Lynn |
| 8,002,765 B2 | 8/2011 | Lopez |
| 8,006,953 B2 | 8/2011 | Bennett |
| 8,016,791 B2 | 9/2011 | Sugiki |
| 8,021,343 B2 | 9/2011 | Nalesso |
| 8,025,646 B2 | 9/2011 | Fukai |
| 8,029,472 B2 | 10/2011 | Leinsing |
| 8,038,647 B2 | 10/2011 | Harding |
| 8,043,263 B2 | 10/2011 | Helgeson |
| 8,043,266 B2 | 10/2011 | Murashita |
| 8,043,316 B2 | 10/2011 | Harding |
| 8,048,031 B2 | 11/2011 | Shaw |
| 8,048,039 B2 | 11/2011 | Carlyon |
| 8,052,646 B2 | 11/2011 | Schweikert |
| 8,052,647 B2 | 11/2011 | Raulerson |
| 8,052,653 B2 | 11/2011 | Gratwohl |
| 8,062,261 B2 | 11/2011 | Adams |
| 8,066,670 B2 | 11/2011 | Cluff |
| 8,075,529 B2 | 12/2011 | Nakajima |
| RE43,141 E | 1/2012 | Halseth |
| 8,088,104 B2 | 1/2012 | Smith |
| 8,096,973 B2 | 1/2012 | Snow |
| 8,100,857 B2 | 1/2012 | Kuracina et al. |
| 8,100,858 B2 | 1/2012 | Woehr et al. |
| 8,105,276 B2 | 1/2012 | Chen |
| 8,123,738 B2 | 2/2012 | Vaillancourt |
| 8,128,594 B1 | 3/2012 | Chang |
| 8,133,207 B2 | 3/2012 | Wilkinson |
| 8,133,209 B2 | 3/2012 | Guala |
| 8,137,321 B2 | 3/2012 | Argentine |
| 8,147,455 B2 | 4/2012 | Butts |
| 8,157,768 B2 | 4/2012 | Haider |
| 8,162,881 B2 | 4/2012 | Lilley, Jr. et al. |
| 8,162,889 B2 | 4/2012 | Swisher |
| 8,162,904 B2 | 4/2012 | Takano |
| 8,197,452 B2 | 6/2012 | Harding |
| 8,206,355 B2 | 6/2012 | Thorne |
| 8,211,070 B2 | 7/2012 | Woehr et al. |
| 8,226,627 B2 | 7/2012 | Fowles |
| 8,231,525 B2 | 7/2012 | Cohen |
| 8,251,950 B2 | 8/2012 | Albert et al. |
| 8,257,322 B2 | 9/2012 | Koehler |
| 2001/0021821 A1 | 9/2001 | Wang |
| 2001/0021827 A1 | 9/2001 | Ferguson |
| 2001/0039401 A1 | 11/2001 | Ferguson |
| 2002/0010434 A1 | 1/2002 | Larsen |
| 2002/0022803 A1 | 2/2002 | Wemmert |
| 2002/0026154 A1 | 2/2002 | Chang |
| 2002/0065488 A1 | 5/2002 | Suzuki |
| 2002/0065489 A1 | 5/2002 | Novacek |
| 2002/0128604 A1 | 9/2002 | Nakajima |
| 2002/0151850 A1 | 10/2002 | Ferguson |
| 2002/0156428 A1 | 10/2002 | Lee |
| 2002/0156430 A1* | 10/2002 | Haarala et al. ............... 604/247 |
| 2003/0060785 A1 | 3/2003 | Lavean |
| 2003/0105431 A1 | 6/2003 | Howell |
| 2003/0114797 A1 | 6/2003 | Vaillancourt |
| 2003/0125676 A1 | 7/2003 | Swenson |
| 2003/0125677 A1 | 7/2003 | Swenson |
| 2003/0130623 A1 | 7/2003 | Chen |
| 2003/0144627 A1 | 7/2003 | Woehr |
| 2003/0181867 A1 | 9/2003 | Bressler |
| 2003/0181869 A1 | 9/2003 | Swenson |
| 2003/0181870 A1 | 9/2003 | Bressler |
| 2003/0181871 A1 | 9/2003 | Wilkinson |
| 2003/0181875 A1 | 9/2003 | Bressler |
| 2003/0195471 A1 | 10/2003 | Woehr |
| 2003/0195479 A1 | 10/2003 | Kuracina |
| 2003/0199827 A1 | 10/2003 | Thorne |

(56) References Cited

U.S. PATENT DOCUMENTS

| | | |
|---|---|---|
| 2003/0216687 A1 | 11/2003 | Hwang |
| 2003/0229316 A1 | 12/2003 | Hwang |
| 2004/0006313 A1 | 1/2004 | Chian |
| 2004/0019334 A1 | 1/2004 | Ohkubo |
| 2004/0039333 A1 | 2/2004 | Lee |
| 2004/0044313 A1 | 3/2004 | Nakajima |
| 2004/0049155 A1 | 3/2004 | Schramm |
| 2004/0078003 A1 | 4/2004 | Smith |
| 2004/0092871 A1 | 5/2004 | Knepshield |
| 2004/0106903 A1 | 6/2004 | Shue |
| 2004/0116857 A1 | 6/2004 | Kiehne |
| 2004/0122378 A1 | 6/2004 | Hsu |
| 2004/0138628 A1 | 7/2004 | Woehr |
| 2004/0147876 A1 | 7/2004 | Maggioni |
| 2004/0171989 A1 | 9/2004 | Horner |
| 2004/0171995 A1 | 9/2004 | Niermann |
| 2004/0186426 A1 | 9/2004 | Allard |
| 2004/0186427 A1 | 9/2004 | Pok |
| 2004/0186434 A1 | 9/2004 | Harding |
| 2004/0204681 A1 | 10/2004 | Thoresen |
| 2004/0225260 A1 | 11/2004 | Villa |
| 2004/0230164 A1 | 11/2004 | Spinks |
| 2004/0236288 A1 | 11/2004 | Howell |
| 2004/0236289 A1 | 11/2004 | Ferguson |
| 2004/0243060 A1 | 12/2004 | Rossi |
| 2004/0243061 A1 | 12/2004 | McGurk |
| 2004/0243066 A1 | 12/2004 | Meyer |
| 2004/0243071 A1 | 12/2004 | Suzuki |
| 2005/0004532 A1 | 1/2005 | Woehr |
| 2005/0027263 A1 | 2/2005 | Woehr |
| 2005/0038385 A1 | 2/2005 | Shen |
| 2005/0038399 A1 | 2/2005 | Suzuki |
| 2005/0043691 A1 | 2/2005 | Ferguson |
| 2005/0049554 A1 | 3/2005 | Chueh |
| 2005/0059933 A1 | 3/2005 | Johnson |
| 2005/0070855 A1 | 3/2005 | Ferguson |
| 2005/0075609 A1 | 4/2005 | Latona |
| 2005/0080378 A1 | 4/2005 | Cindrich |
| 2005/0085745 A1 | 4/2005 | Kitta |
| 2005/0096599 A1 | 5/2005 | Crawford |
| 2005/0119627 A1 | 6/2005 | Crawford |
| 2005/0137528 A1 | 6/2005 | Wilkinson |
| 2005/0137535 A1 | 6/2005 | Gollobin |
| 2005/0159706 A1 | 7/2005 | Wilkinson |
| 2005/0182362 A1 | 8/2005 | Sircom |
| 2005/0215951 A1 | 9/2005 | Saulenas |
| 2005/0234408 A1 | 10/2005 | Chong |
| 2005/0240150 A1 | 10/2005 | Gordon |
| 2005/0267412 A1 | 12/2005 | Wilkinson |
| 2006/0058742 A1 | 3/2006 | Cha |
| 2006/0074384 A1 | 4/2006 | Kohler |
| 2006/0079808 A1 | 4/2006 | Allard |
| 2006/0084916 A1 | 4/2006 | Lo |
| 2006/0106339 A1 | 5/2006 | Mastorakis |
| 2006/0106340 A1 | 5/2006 | Goossens |
| 2006/0116638 A1 | 6/2006 | Woehr |
| 2006/0155245 A1 | 7/2006 | Woehr |
| 2006/0161108 A1 | 7/2006 | Mogensen |
| 2006/0161116 A1 | 7/2006 | Willis |
| 2006/0184115 A1 | 8/2006 | Saled |
| 2006/0189934 A1 | 8/2006 | Kuracina |
| 2006/0200195 A1 | 9/2006 | Yang |
| 2006/0217655 A1 | 9/2006 | Vitullo |
| 2006/0229554 A1 | 10/2006 | Lou |
| 2006/0229556 A1 | 10/2006 | Pressly, Sr. |
| 2006/0229563 A1 | 10/2006 | O'Reagan |
| 2006/0253074 A1 | 11/2006 | Thayer |
| 2006/0253076 A1 | 11/2006 | Butts |
| 2006/0264827 A1 | 11/2006 | Whang |
| 2006/0264828 A1 | 11/2006 | Woehr |
| 2007/0005013 A1 | 1/2007 | Lai |
| 2007/0005014 A1 | 1/2007 | Lin |
| 2007/0016139 A1 | 1/2007 | Breitweiser |
| 2007/0038179 A1 | 2/2007 | Bialecki |
| 2007/0038182 A1 | 2/2007 | Bialecki |
| 2007/0038183 A1 | 2/2007 | Bialecki |
| 2007/0038184 A1 | 2/2007 | Bialecki |
| 2007/0038185 A1 | 2/2007 | Albert |
| 2007/0038186 A1 | 2/2007 | Sutton |
| 2007/0038187 A1 | 2/2007 | Albert |
| 2007/0038188 A1 | 2/2007 | Bialecki |
| 2007/0073221 A1 | 3/2007 | Bialecki |
| 2007/0073222 A1 | 3/2007 | Lilley, Jr. |
| 2007/0073225 A1 | 3/2007 | Lee |
| 2007/0078390 A1 | 4/2007 | Cing-hong |
| 2007/0078397 A1 | 4/2007 | Weststrate |
| 2007/0078404 A1 | 4/2007 | Wu |
| 2007/0078405 A1 | 4/2007 | Lai |
| 2007/0078407 A1 | 4/2007 | Huang |
| 2007/0083162 A1 | 4/2007 | O'Reagan |
| 2007/0083167 A1 | 4/2007 | Smith |
| 2007/0100296 A1 | 5/2007 | Hwang |
| 2007/0100297 A1 | 5/2007 | Woehr |
| 2007/0106231 A1 | 5/2007 | Snow |
| 2007/0118082 A1 | 5/2007 | Mori |
| 2007/0135764 A1 | 6/2007 | Chen |
| 2007/0149893 A1* | 6/2007 | Heske et al. .................. 600/566 |
| 2007/0156093 A1 | 7/2007 | Woehr |
| 2007/0156100 A1 | 7/2007 | Moesli |
| 2007/0161950 A1 | 7/2007 | Carlyon |
| 2007/0179443 A1 | 8/2007 | Johnson aka Mindes |
| 2007/0179446 A1 | 8/2007 | Carrez |
| 2007/0197964 A1 | 8/2007 | Hsu |
| 2007/0197965 A1 | 8/2007 | Hsu |
| 2007/0197966 A1 | 8/2007 | Lee |
| 2007/0197967 A1 | 8/2007 | Lee |
| 2007/0219492 A1 | 9/2007 | Lucas |
| 2007/0232998 A1 | 10/2007 | Yang |
| 2007/0250003 A1 | 10/2007 | Bare |
| 2007/0255212 A1 | 11/2007 | Smith |
| 2007/0270753 A1 | 11/2007 | Kulli |
| 2007/0282268 A1 | 12/2007 | Mayse |
| 2008/0021388 A1 | 1/2008 | Schwarzich |
| 2008/0027381 A1 | 1/2008 | Smith |
| 2008/0065015 A1 | 3/2008 | Fiser |
| 2008/0065025 A1 | 3/2008 | Jenkins |
| 2008/0071213 A1 | 3/2008 | Sircom |
| 2008/0071222 A1 | 3/2008 | Rhad |
| 2008/0086089 A1 | 4/2008 | Isaacson |
| 2008/0097304 A1 | 4/2008 | Thorne |
| 2008/0097342 A1 | 4/2008 | Gordin |
| 2008/0097343 A1 | 4/2008 | Woehr |
| 2008/0097344 A1 | 4/2008 | McKinnon |
| 2008/0097345 A1 | 4/2008 | Ferguson |
| 2008/0103449 A1 | 5/2008 | Murashita |
| 2008/0108944 A1 | 5/2008 | Woehr |
| 2008/0115845 A1 | 5/2008 | Leuliet |
| 2008/0119795 A1 | 5/2008 | Erskine |
| 2008/0140011 A1 | 6/2008 | Hager |
| 2008/0147003 A1 | 6/2008 | Menzi |
| 2008/0154195 A1 | 6/2008 | Huang |
| 2008/0177238 A1 | 7/2008 | Follman |
| 2008/0243086 A1 | 10/2008 | Hager |
| 2008/0249478 A1 | 10/2008 | Ishikura |
| 2008/0249480 A1 | 10/2008 | Riesenberger |
| 2008/0283789 A1 | 11/2008 | Rubio |
| 2008/0312596 A1 | 12/2008 | Murashita |
| 2008/0319387 A1* | 12/2008 | Amisar et al. ............. 604/95.04 |
| 2009/0005743 A1 | 1/2009 | Vaillancourt |
| 2009/0012480 A1 | 1/2009 | Moulton |
| 2009/0048566 A1 | 2/2009 | Ferguson |
| 2009/0054852 A1 | 2/2009 | Takano |
| 2009/0082732 A1 | 3/2009 | Hillman |
| 2009/0088696 A1 | 4/2009 | Harding |
| 2009/0093771 A1 | 4/2009 | Hwang |
| 2009/0131872 A1* | 5/2009 | Popov ..................... 604/164.08 |
| 2009/0131876 A1 | 5/2009 | Coyne |
| 2009/0137958 A1 | 5/2009 | Erskine |
| 2009/0143737 A1 | 6/2009 | Kobayashi |
| 2009/0157013 A1 | 6/2009 | Wong |
| 2009/0163861 A1 | 6/2009 | Carlyon |
| 2009/0171285 A1 | 7/2009 | Wang |
| 2009/0177167 A1 | 7/2009 | Kuracina |
| 2009/0182280 A1 | 7/2009 | Glowacki |

(56) References Cited

U.S. PATENT DOCUMENTS

| | | |
|---|---|---|
| 2009/0216153 A1 | 8/2009 | Srivatsa |
| 2009/0216201 A1 | 8/2009 | Meehan |
| 2009/0221961 A1* | 9/2009 | Tal et al. ............ 604/103.06 |
| 2009/0227956 A1 | 9/2009 | Emmott |
| 2009/0281499 A1 | 11/2009 | Harding |
| 2009/0281506 A1 | 11/2009 | Mathias |
| 2009/0287154 A1 | 11/2009 | Harding |
| 2009/0292260 A1 | 11/2009 | Vaillancourft |
| 2009/0292261 A1 | 11/2009 | Greene |
| 2009/0306591 A1 | 12/2009 | Amisar |
| 2009/0312711 A1 | 12/2009 | Brimhall |
| 2010/0063455 A1 | 3/2010 | Moyer |
| 2010/0069840 A1 | 3/2010 | Suresh |
| 2010/0082002 A1 | 4/2010 | Baid |
| 2010/0087787 A1 | 4/2010 | Woehr |
| 2010/0094171 A1* | 4/2010 | Conway et al. ............ 600/575 |
| 2010/0106092 A1 | 4/2010 | Tanabe |
| 2010/0114035 A1 | 5/2010 | Schubert |
| 2010/0114036 A1 | 5/2010 | Steyn |
| 2010/0137815 A1 | 6/2010 | Kuracina |
| 2010/0191188 A1 | 7/2010 | Harding |
| 2010/0191189 A1 | 7/2010 | Harding |
| 2010/0198152 A1 | 8/2010 | Haindl |
| 2010/0204652 A1 | 8/2010 | Morrissey |
| 2010/0204654 A1 | 8/2010 | Mulholland |
| 2010/0222739 A1 | 9/2010 | Klippenstein |
| 2010/0222745 A1 | 9/2010 | Burkholz |
| 2010/0222746 A1 | 9/2010 | Burkholz |
| 2010/0228197 A1 | 9/2010 | Murashita |
| 2010/0234804 A1 | 9/2010 | Hiejima |
| 2010/0241087 A1 | 9/2010 | Moulton |
| 2010/0249707 A1 | 9/2010 | Woehr |
| 2010/0286611 A1 | 11/2010 | Schraga |
| 2010/0298770 A1 | 11/2010 | Rubinstein |
| 2010/0324484 A1 | 12/2010 | Smith |
| 2010/0331781 A1 | 12/2010 | Millerd |
| 2011/0015573 A1 | 1/2011 | Maan |
| 2011/0015579 A1 | 1/2011 | Swisher |
| 2011/0024664 A1 | 2/2011 | Burnard |
| 2011/0054398 A1 | 3/2011 | Djordjevic |
| 2011/0054402 A1 | 3/2011 | Tanabe |
| 2011/0054403 A1 | 3/2011 | Tanabe |
| 2011/0060286 A1 | 3/2011 | Tanabe |
| 2011/0060294 A1 | 3/2011 | Baid |
| 2011/0066107 A1 | 3/2011 | Stephens |
| 2011/0066197 A1 | 3/2011 | Jaax |
| 2011/0092914 A1 | 4/2011 | Clayson |
| 2011/0098641 A1 | 4/2011 | Haider |
| 2011/0118673 A1 | 5/2011 | Dringenberg |
| 2011/0125056 A1 | 5/2011 | Merchant |
| 2011/0152782 A1 | 6/2011 | Jones |
| 2011/0152832 A1 | 6/2011 | Foshee |
| 2011/0160662 A1 | 6/2011 | Stout |
| 2011/0160663 A1 | 6/2011 | Stout |
| 2011/0160675 A1 | 6/2011 | Ruan |
| 2011/0208124 A1 | 8/2011 | Rhad |
| 2011/0208126 A1 | 8/2011 | Riemelmoser |
| 2011/0208133 A1 | 8/2011 | Woehr |
| 2011/0213307 A1 | 9/2011 | Kawai |
| 2011/0264037 A1 | 10/2011 | Foshee |
| 2011/0264040 A1 | 10/2011 | Li |
| 2011/0275991 A1 | 11/2011 | Thayer |
| 2011/0282285 A1 | 11/2011 | Blanchard |
| 2011/0282286 A1 | 11/2011 | Argentine |
| 2011/0301542 A1 | 12/2011 | Schwartz |
| 2011/0301551 A1 | 12/2011 | Koehler |
| 2011/0319820 A1 | 12/2011 | Teoh |
| 2012/0016301 A1 | 1/2012 | Stout |
| 2012/0016302 A1 | 1/2012 | Stout et al. |
| 2012/0022498 A1 | 1/2012 | Smith |
| 2012/0035552 A1 | 2/2012 | Woehr |
| 2012/0041374 A1 | 2/2012 | Lee |
| 2012/0046620 A1 | 2/2012 | Woehr et al. |
| 2012/0046621 A1 | 2/2012 | Vaillancourt |
| 2012/0059323 A1 | 3/2012 | Moberg |
| 2012/0059325 A1 | 3/2012 | Cluff et al. |
| 2012/0078200 A1 | 3/2012 | Woehr |
| 2012/0130321 A1 | 5/2012 | Woehr |
| 2012/0136311 A1 | 5/2012 | Knutsson |
| 2012/0143138 A1 | 6/2012 | King |
| 2012/0143151 A1 | 6/2012 | Low |
| 2012/0184910 A1 | 7/2012 | Woehr |
| 2012/0197201 A1 | 8/2012 | Tanabe |
| 2012/0215179 A1 | 8/2012 | Halili |
| 2012/0220956 A1 | 8/2012 | Kuracina et al. |
| 2012/0220957 A1 | 8/2012 | Kuracina et al. |
| 2012/0277679 A1 | 11/2012 | Steube |
| 2013/0030370 A1 | 1/2013 | Walker et al. |
| 2013/0079720 A1 | 3/2013 | Finnestad et al. |
| 2013/0096504 A1 | 4/2013 | Walker et al. |

FOREIGN PATENT DOCUMENTS

| | | |
|---|---|---|
| JP | 2003-199822 | 7/2003 |
| JP | 2005237638 A | 9/2005 |
| WO | WO 2010/061405 | 6/2010 |
| WO | WO 2011/036574 | 3/2011 |
| WO | WO 2011/154767 | 12/2011 |
| WO | WO 2012/014018 | 2/2012 |

OTHER PUBLICATIONS

European Search Report from European Application No. EP 10008423 dated Dec. 6, 2010.
U.S. Appl. No. 13/616,464, filed Sep. 14, 2012, Tremblay.
European Search Report dated Jul. 26, 2012 in copending European Appln. 12165851.
International Search Report dated Dec. 17, 2012 in copending International Application No. PCT/2012/055295.
International Search Report dated Dec. 19, 2012 in copending International Application No. PCT/US2012/056979.
International Search Report dated Jan. 16, 2013 in copending International Application No. PCT/US2012/060240.
Mexican Office Action dated May 12, 2014 issued in Mexican Application No. MX/a/2009/003466.
Canadian Office Action dated Sep. 19, 2013 in Canadian Application No. 2,664,507.

* cited by examiner

NEEDLE TIP PROTECTOR

CROSS-REFERENCE TO RELATED APPLICATION

This application is a national stage entry of PCT/US07/21794, filed Oct. 12, 2007, which is based on and claims the benefit of priority to Japanese Patent Application 2006-278436, filed Oct. 12, 2006.

BACKGROUND

1. Technical Field

The invention relates to a needle tip protector device which is mounted about a puncturing part of a puncturing needle after the puncturing needle has been removed from an indwelling needle.

2. Background of the Art

It is conventional to use an indwelling needle to supply a predetermined medicinal liquid and the like to the blood vessels of a patient to perform a medical procedure, such as artificial dialysis. The indwelling needle used in such a case includes a cannula for positioning a needle tip within the blood vessel of the patient and a body portion connected to the basal end portion of the cannula. In order to position the tip end of the cannula within a blood vessel, a puncturing needle is provided to pierce the body to facilitate smooth manipulation of the cannula into the blood vessel. When the manipulation described above is carried out, the puncturing needle is inserted into the indwelling needle such that the tip of the puncturing needle projects slightly from the tip end portion of the cannula. In that condition, the cannula together with the puncturing needle is inserted into the blood vessel. After the cannula is positioned within the blood vessel, the puncturing needle is pulled out of the indwelling needle and blood vessel and the rear end portion of the indwelling needle is connected to a tube member or the like for supplying the predetermined medicinal liquid to or from the blood vessel.

Such an indwelling needle set includes a needle tip protector for preventing the needle tip of the puncturing needle which is removed from the cannula from injuring the patient or the like (for example, see Patent Literature 1). The needle tip protector is formed by a cylinder comprising one end having an opening having a large inner diameter and the other end having an opening having a small inner diameter. The tip end portion of the puncturing needle to be protected by the needle tip protector is formed so as to have a size to allow passage of the puncturing needle through the large diameter opening of the needle tip protector but prevent passage of the puncturing needle through the small diameter opening of the needle tip protector. A rear portion of the puncturing needle is formed or is dimensioned to permit insertion through the small diameter opening. Therefore, when the puncturing needle is pulled rearwardly relative to the needle tip protector while the large diameter opening is opposed to the tip end portion of the puncturing needle and the rear portion of the puncturing needle is positioned though the small diameter opening, the needle tip protector will be engaged by the tip end portion of the puncturing needle such that the tip of the puncturing needle is covered by the needle tip protector.

Although, the conventional needle tip protector described above can not be removed from the tip end portion of the puncturing needle, the protector has a tendency to move towards the rear portion of the puncturing needle thus, exposing the tip end portion of the puncturing needle. Therefore, a needle tip protector capable of securely covering the tip end portion of the puncturing needle by fixing it to the tip end portion of the puncturing needle has been developed. One drawback of such a needle tip protector, however, is that the operationality of the needle tip protector may be negatively affected because the combination of the puncturing needle and the cannula and the like installed into the indwelling needle increases the length of the indwelling needle set.

SUMMARY

The present disclosure provides a needle tip protection device which includes a needle tip protector body having a front portion configured to receive the rear end of an outer needle and a rear portion defining a rearwardly extending engagement tube defining a hole. A stopper member is supported within the rear portion of the needle tip protector body. The stopper member is movable from a first position obstructing the hole of the engagement tube to a second position providing access to the hole of the engagement tube. A protecting sleeve is slidably positioned within the hole of the engagement tube between an advanced position located substantially within the needle tip protector body and a retracted position extending rearwardly from the needle tip protector body through the hole of the engagement tube. The protecting sleeve has a forward end and a rear end. The rear end of the protecting sleeve is dimensioned to be slidably received in the hole of the engagement tube and the forward end of the protecting sleeve is dimensioned to prevent passage of the forward end of the protecting sleeve through the hole of the engagement tube. The protecting sleeve defines a bore having a forward opening having a first diameter and a rear opening having a second diameter smaller than the first diameter.

In one embodiment, the stopper member defines a hole which is aligned with the hole in the engagement tube when the stopper member is in its second position and misaligned with the hole in the engagement tube when the stopper member is in its first position. The hole in the stopper member is dimensioned to permit passage of the protector sleeve. The stopper member may be urged to its first position by a spring, e.g., a coil spring.

In one embodiment, the needle tip protector body further includes a diaphragm separating the front portion of the needle tip protector body and the rear portion of the needle tip protector body. The diaphragm defines an insertion hole which is aligned with the hole in the engagement tube.

The stopper member may include an engagement piece configured to secure the needle tip protector body to a needle housing of an indwelling needle set when the stopper member is in the second position. The engagement piece of the stopper member can include an engagement claw.

In one embodiment, the protecting sleeve extends through the hole in the stopper member when the protecting sleeve is in the advanced position and engages the walls of the sleeve defining the hole in the stopper member to retain the stopper member in its second position. The walls of the sleeve defining the hole in the stopper member may be convex.

In one embodiment, the hole in the engagement tube defines a stepped bore, wherein a rear portion of the stepped bore has a diameter which is smaller than a diameter of a forward portion of the stepped bore. A step may be defined between the forward portion of the stepped bore and the rear portion of the stepped bore, such that the rear end of the protecting sleeve engages the step when the protecting sleeve is in its retracted position.

The present disclosure also provides an indwelling needle set including an outer needle having a cannula and a housing body defining a chamber. An elastic valve is supported within the chamber. An inner needle has a forward puncturing end and a rear end. The forward puncturing end has an enlarged diameter portion. The needle set also includes a needle tip protection device comprising a needle tip protector body having a front portion configured to receive the rear end of the housing of the outer needle and a rear portion defining a rearwardly extending engagement tube defining a hole. A stopper member is supported within the rear portion of the needle tip protector body, the stopper member is movable from a first position obstructing the hole of the engagement tube to a second position providing access to the hole of the engagement tube. A protecting sleeve is slidably positioned within the hole of the engagement tube between a advanced position located substantially within the needle tip protector body and a retracted position extending rearwardly from the needle tip protector body through the hole of the engagement tube. The protecting sleeve has a forward end and a rear end, the rear end is dimensioned to be slidably received in the hole of the engagement tube and the forward end is dimensioned to prevent passage of the forward end of the protecting sleeve through the hole of the engagement tube. The protecting sleeve defines a bore having a forward opening having a first diameter and a rear opening having a second diameter smaller than the first diameter. The inner needle is slidably positioned within the protecting sleeve. The enlarged diameter portion of the inner needle is greater in diameter than the second diameter of the rear opening of the protecting sleeve such that the inner needle cannot be withdrawn from the rear end of the protecting sleeve.

In one embodiment, a tube insertion portion is movably supported within the housing. The tube insertion portion defines a bore and is movable from a rearward position to a forward position, wherein an insertion end of the tube insertion portion extends through an opening in the elastic valve. The tube insertion portion may be urged towards its rearward position by a spring.

In one embodiment, the housing body includes an external thread adapted to engage a tube member for supplying medicinal fluid to the needle set. The inner needle may include a hub member supported on a rear end of the inner needle.

In one embodiment, the stopper member defines a hole which is aligned with the hole in the engagement tube when the stopper member is in its second position and misaligned with the hole in the engagement tube when the stopper member is in its first position. The hole in the stopper member is dimensioned to permit passage of the protector sleeve. The stopper member may be urged to its first position by a coil spring.

In one embodiment, the needle tip protector body includes a diaphragm separating the front portion of the needle tip protector body and the rear portion of the needle tip protector body. The diaphragm defines an insertion hole which is aligned with the hole in the engagement tube.

The stopper member may include an engagement piece configured to secure the needle tip protector body to the housing body of the outer needle when the stopper member is in the second position. The engagement piece of the stopper member can be in the form of an engagement claw and the housing body of the outer needle can include a projection. The engagement claw is positioned to engage the projection when the stopper member is in its second position to secure the needle tip protector body to the housing body and to disengage the projection when the stopper member is in its first position to detach the needle tip protector body from the housing body.

In one embodiment, the protecting sleeve extends through the hole in the stopper member when the protecting sleeve is in the advanced position and engages walls of the sleeve defining the hole in the stopper member to retain the stopper member in its second position. The walls of the sleeve defining the hole in the stopper member may be convex.

In one embodiment, the hole in the engagement tube defines a stepped bore. A rear portion of the stepped bore has a diameter which is smaller than a diameter of a forward portion of the stepped bore. A step may be defined between the forward portion of the stepped bore and the rear portion of the stepped bore, wherein the rear end of the protecting sleeve engages the step when the protecting sleeve is in its retracted position.

BRIEF DESCRIPTION OF THE DRAWINGS

Various embodiments of the presently disclosed needle tip protection device in association with an indwelling needle set are disclosed herein with reference to the drawings, wherein.

DETAILED DESCRIPTION

Figure 1:
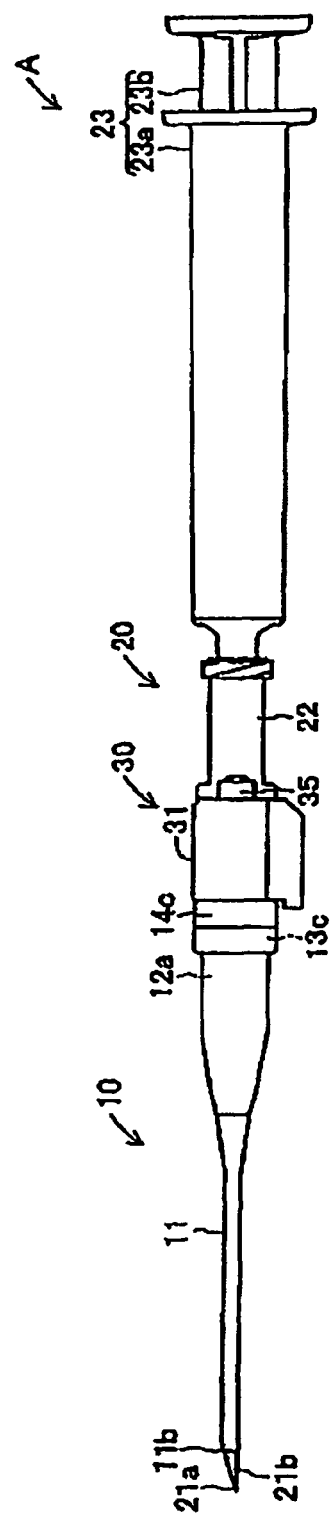
FIG. 1 is a side view illustrating an indwelling needle set including one embodiment of the presently disclosed needle tip protector device.
Figure 2:
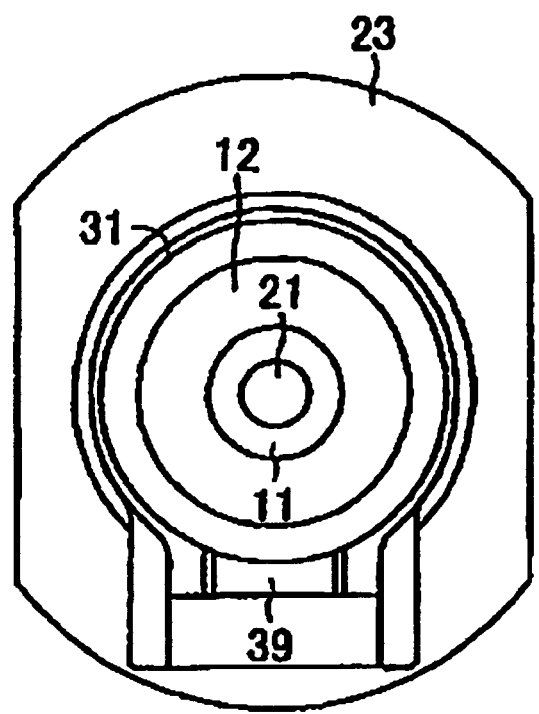
FIG. 2 is a front view of the indwelling needle set shown in FIG. 1.
Figure 3:
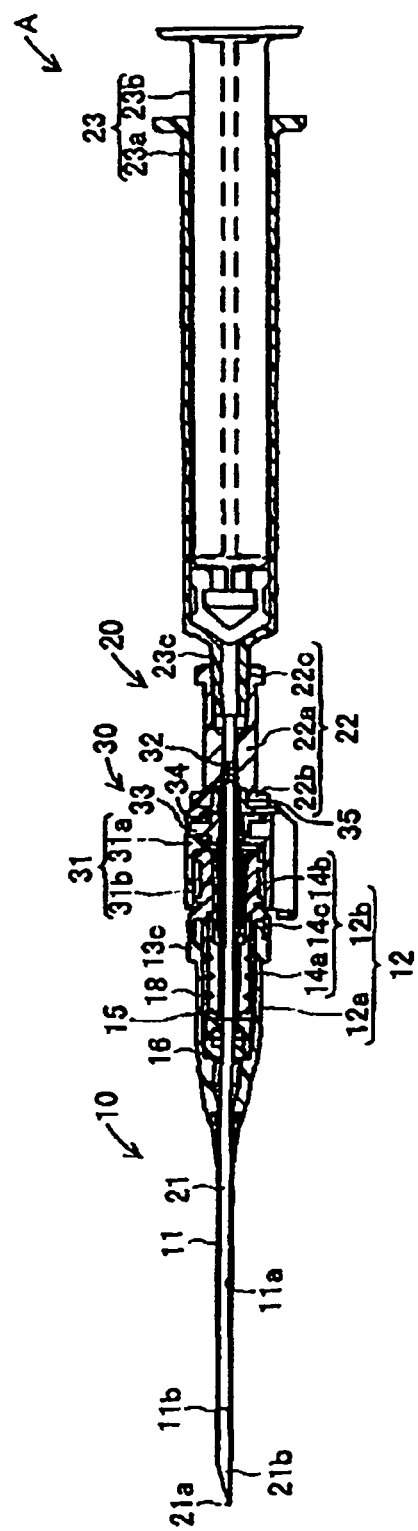
FIG. 3 is a cross sectional view of the indwelling needle set shown in FIG. 1.
Figure 4:
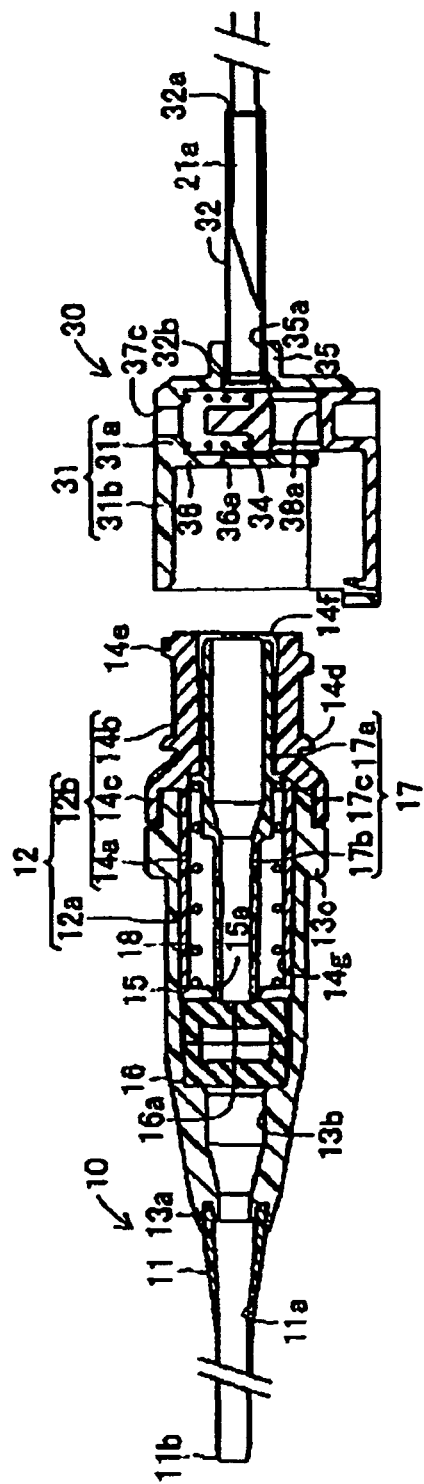
FIG. 4 is a cross sectional view of the indwelling needle set shown in FIG. 1 with the inner needle withdrawn from the outer needle and the needle tip protector device separated from the outer needle.

The needle tip protector device in accordance with the present disclosure will now be explained in detail with the reference to the drawings. FIGS. 1 to 13 show an indwelling needle set A including one embodiment of the presently disclosed needle tip protector device 30. The indwelling needle set A comprises an outer needle assembly 10 to be positioned within a blood vessel of a patient (indwelling needle), an inner needle assembly 20 dimensioned to be inserted into the outer needle 10 and having a sharpened tip end portion configured to penetrate into the body of a patient, and the tip protector device 30. The outer needle assembly 10, as shown in FIG. 4, includes a narrow tube like cannula 11 and a housing 12 connected to the basal end portion (the rear portion positioned to the right side in FIG. 4) of the cannula 11.

The cannula 11 defines a lumen 11a (FIG. 3) which forms a flow path that extends from the tip end portion of cannula 11 to the rear end portion of cannula 11. In use, the tip end portion 11b of the cannula 11 is positioned within the blood vessel of a patient for removing blood from or supplying medicinal solutions or the like to a blood vessel. Also, the basal end portion of the cannula 11 is formed such that the diameter thereof gradually increases towards the rear end portion of cannula 11. The housing 12 defines a chamber and comprises a housing body 12a connected to the basal end portion of the cannula 11 and a housing tube 12b (FIG. 3) positioned within and along the rear end of the housing body 12a.

A front end portion of the housing body 12a is formed into a tapered cylinder in which the size thereof is gradually decreased from its rear end to its front end. The front end portion of housing body 12a is provided with an annular engagement groove 13a (FIG. 4) on its tip end portion for fixing the basal end portion of the cannula 11 to the front end of housing body 12a. The rear portion of the housing body 12a is formed into a cylinder having a diameter defining a space or cavity 13b. Space 13b includes a generally tapered front portion and a rear end having a generally constant diameter. The outer profile of the housing body 12a has a generally constant diameter portion and a slightly wider ring shaped projection 13c which is formed along the circumference at the rear end of the outer peripheral surface of the housing body 12a.

The housing tube 12b comprises an inner tube portion 14a provided within the housing body 12a which contacts the rear portion of the inner peripheral surface of the housing body 12a and a tube portion 14b which engages and extends rearwardly from the rear end of the housing body 12a. Also, an annular projection 14c is provided on the front end of the outer peripheral portion of the tube portion 14b. The annular projection 14c is configured so as to cover the outer peripheral surface of the rear end of the housing 12a. The housing tube 12b is connected to the housing body 12 by sandwiching the rear end portion of the housing body 12a between the basal end portion of the inner tube portion 14a and the projection 14c.

When housing tube 12b is attached to housing body 12a, the tip end portion of the projection 14c contacts the rear end portion of the projection 13c of the housing body 12a. An outer peripheral surface 14b of housing tube 12b includes a projection 14d and an external thread 14e. Projection 14d is located on the forward end of tube portion 14b and external thread 14e is located on the rear end of tube portion 14b. An inner peripheral surface 14f of the tube 12b has a tapered surface is gradually decreased in diameter from the rear end opening to the forward end opening. The diameter of an inner peripheral surface 14g of housing tube 12b is provided so as to be larger than the diameter of the inner peripheral surface 14f of housing tube 12b. Therefore, a differential step is formed between the inner peripheral surface 14g and the inner peripheral surface 14f.

A partition wall 15 is positioned at the forward end portion of the inner tube 14a in the inner peripheral surface 14g of the housing body 12a and a valve 16 is provided on the forward side of the partition wall 15 in the space 13b of the housing body 12a. A tube insertion portion 17 is provided within the housing tube 12b adjacent the rear side of the partition wall 15. The partition wall 15 is formed by a disc having a hole 15a at the center thereof for communicating the front portion of the space 13b with the rear portion of space 13b in the housing body 12a.

In one embodiment, the valve 16 is formed by an elastic isoprene rubber and comprises a chamber type valve including a pair of circular box bodies each having an opened surface opposed to the other. The valve 16 also includes an opening and closing hole 16a along the central axis of the valve 16. Through hole 16a, a predetermined narrow member can be inserted. When the narrow member is not inserted through hole 16a, because of the elastic properties of valve 15, the valve 16 is maintained in an occluding condition as shown in FIG. 3. On the other hand, when a puncturing needle 21 or the like as described below is inserted through hole 16a, as shown in FIG. 3, the valve 16 tightly contacts the outer peripheral surface of the puncturing needle 21 or the like to provide a liquid tight seal about the puncturing needle 21.

The tube insertion portion 17 comprises a two stepped tube having an axial length almost the same as that of the housing tube 12b. The tube insertion portion 17 includes a basal portion 17a having a large diameter and an insertion end 17b extending forwardly from the front surface of the basal portion 17a having a smaller diameter. A spring receiving portion 17c of tube insertion portion 17 includes an annular projection. The annular projection is formed on the outer peripheral surface of the basal portion 17a of tube insertion portion 17. The spring receiving portion 17c is axially movably positioned within the inner peripheral surface 14g of the housing tube 12b and contacts the step portion defined between the inner peripheral surface 14g and the inner peripheral surface 14f, to prevent the portion 17c from moving beyond the inner peripheral surface 14f of tube 14b.

When the spring receiving portion 17c engages the step portion between the inner peripheral surface 14g and the inner peripheral surface 14f, the tip end portion of the insertion end 17b of tube insertion portion 17 is located within the hole 15a of the partition wall 15 and the basal portion 17a of tube insertion portion 17 is positioned near the rear end portion of the housing tube 12b. The insertion end 17b is dimensioned and configured such that it can be inserted into the hole 15a of partition wall 15 and passed through the hole 16a of the valve 16 in a liquid tight manner. When insertion end 17b is passed through the hole 16a of the valve 16, the inside of the tube insertion portion 17 communicates with the lumen 11a of the cannula 11 through the space 13b. A coil spring 18 is provided between the partition wall 15 and the spring receiving portion 17c of insertion portion 17 in the inner tube 14a so as to surround the outer periphery of the insertion end 17b of insertion portion 17 and the forward end of the basal portion 17a to urge the tube insertion portion 17 rearwardly. In its rearward position, tube insertion portion 17 is spaced rearwardly of valve 16.

Figure 5:
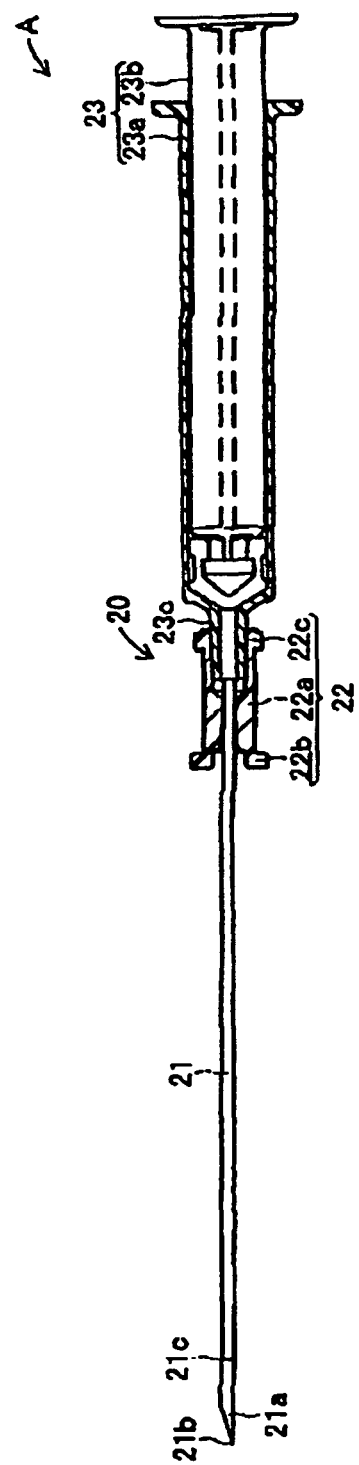
FIG. 5 is a cross sectional view illustrating the inner needle assembly of the indwelling needle set shown in FIG. 1 connected to a syringe.

The inner needle assembly 20, as shown in FIG. 5, comprises the puncturing needle 21 which can be made of stainless steel, and a hub 22 which is fixed to the basal end portion (rear end portion positioned to the right side in FIG. 5) of the puncturing needle 21. A syringe 23 is connected to the hub 22. The puncturing needle 21 includes a narrow tubular hypodermic needle having a sharp tip end portion 21b formed on the forward end of a puncturing portion 21a. Sharp tip end portion 21a is formed by providing an inclining or tapering puncturing portion 21a. A step portion 21c (the engagement portion) is formed at the rear end portion of the puncturing portion 21a at a forward end of puncturing needle 21. In one embodiment, the diameter of the puncturing portion 21a, which is positioned forwardly of step portion 21c, is slightly larger than the diameter of a rear end portion, i.e., the portion of puncturing needle 21 positioned rearwardly of step portion 21c.

Sharp tip end portion 21b of the puncturing needle 21 is provided to facilitate smooth insertion of needle 21 and the tip end portion 11b of the cannula 11 into the blood vessel of the patient. Thus, the puncturing needle 21 is inserted into the outer needle 10 from the rear end portion of the outer needle 10 through the needle tip protector 30, as described below, such that the puncturing portion 21a of needle 21 projects outwardly from the opening of the tip end portion 11b of the cannula 11. When indwelling needle set A is assembled for use, the puncturing portion 21a of the puncturing needle 21 is passed through the inside of the needle tip protector 30, the inside of the tubular insertion portion 17, the hole 16a of the valve 16, the space 13b of the housing body 12a and the lumen 11a of the cannula 11 to project outwardly from the tip end portion 11b of the cannula 11.

The hub 22 of inner needle assembly 20 is configured as a holding portion for grasping the inner needle 20. Hub 22 can be formed from a transparent resin material which is fixed to the puncturing needle 21 so as to cover the outer periphery of the basal end portion of the puncturing needle 21. Hub 22 comprises a hub body 22a positioned at a central portion of hub 22 for fixing the puncturing needle 21 to hub body 22a. Hub 22 also includes a flange shaped receiving portion 22b formed at a forward end of the hub body 22a which is dimensioned to maintain a predetermined distance between the periphery of the puncturing needle 21 and flange portion 22b, and a cylindrical female lure part 22c including a recess formed at the rear side of the hub body 22a. The syringe 23 is attached to the female lure part 22c of hub 22. The syringe 23 is comprised of a cylinder part 23a and a piston part 23b. The syringe 23 is connected to the inner needle assembly 20 by inserting a male lure part 23c formed at the tip end portion of the cylinder part 23a of syringe 23 into the female lure part 22c of hub 22.

Figure 6:
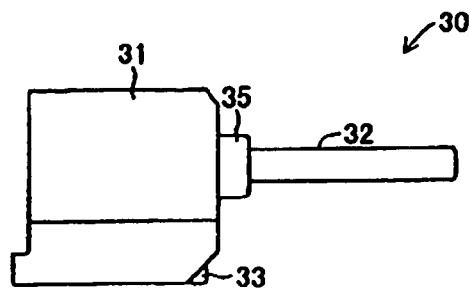
FIG. 6 is a side view of the needle tip protector device of the indwelling needle set shown in FIG. 1.
Figure 7:
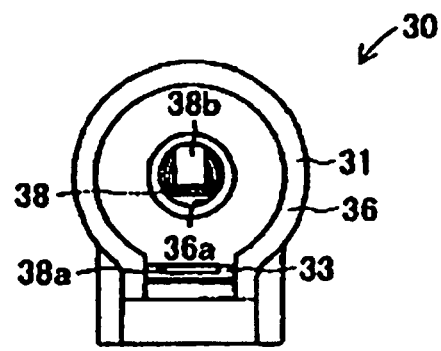
FIG. 7 is a front view of the needle tip protector device shown in FIG. 6.
Figure 8:
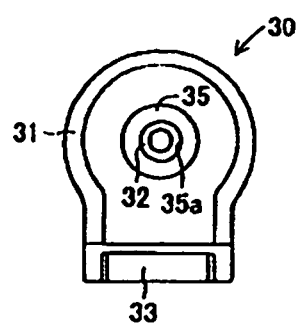
FIG. 8 is a backside view of the needle tip protector device shown in FIG. 6.
Figure 11:
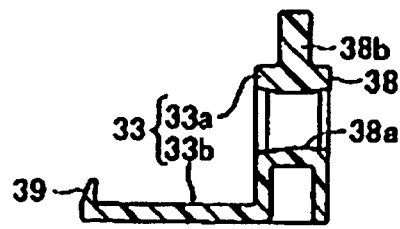
FIG. 11 is a cross sectional view of the stopper member of the needle tip protector device shown in FIG. 6.
Figure 12:
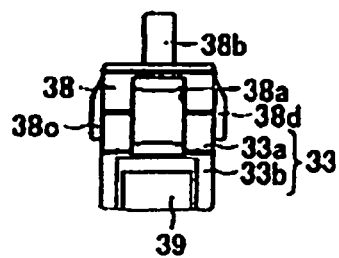
FIG. 12 is a front view of the stopper member shown in FIG. 11.

The needle tip protector 30 shown in FIGS. 6 to 8 releasably engages the outer periphery of tube portion 14b of housing 12. When needle set A is assembled, the puncturing needle 21 of the inner needle 20 is passed through the needle tip protector device 30 and extends to the tip end side of the cannula 11. The needle tip protector 30 comprises a protector body 31 which is configured to be mounted to the tube portion 14b of housing 12. A needle tip protecting sleeve 32 is mounted to the protector body 31 and is movable forwardly and backwardly from a position extending into the protector body 31 to a position extending rearwardly from the protector body 31. A stopper member 33 FIGS. 11 and 12 is attached to the protector body 31 so as to be upwardly and downwardly moveable and a biasing member, e.g., a coil spring 34 is positioned to urge the stopper member 33 downwardly as illustrated in FIG. 4.

Figure 9:
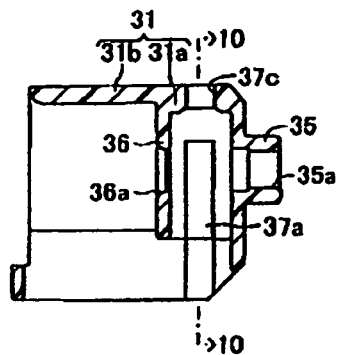
FIG. 9 is a cross sectional view of the needle tip protector body of the needle tip protector device shown in FIG. 6.

The protector body 31 includes a generally box shaped case member which is opened at it forward end. A rear wall of body 31 is provided with an engagement tube 35 which extends outwardly and backwardly from the rear wall. An upper side of protector body 31 is formed into almost a cylindrical shape (FIG. 10) which corresponds with the outer profile of the tube portion 14b to which protector body 31 is engaged. The lower side portion of protector body 31 includes a pair of substantially parallel, spaced wall portions. The engagement tube 35, as shown in FIG. 9, defines an engagement hole 35a having a diameter at its forward end (the portion positioned at the inside of the protector body 31) that is slightly larger than the diameter of engagement hole 35a at its rear end. A step is defined between the forward end and the rear end of hole 35a.

Protector body 31 includes a diaphragm 36 located towards the rear wall of protector body 31 for partitioning the upper side portion of the protector body 31 into a front portion and a rear portion. The rear portion of the protector body 31 forms a stopper member receiving portion 31a. The forward portion of protector body 31 forms a covering portion 31b for covering the tube portion 14b. The diaphragm 36 also includes an insertion hole 36a which opposes engagement tube 35 and has a diameter generally the same as the large diameter portion of the engagement hole 35a. Insertion hole 36a is provided so as to be coaxial with the engagement hole 35a.

Figure 10:
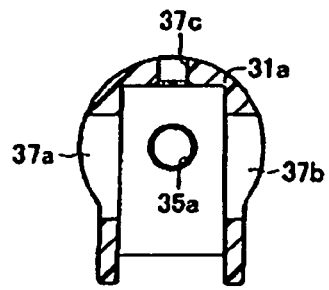
FIG. 10 is a cross sectional view along section lines 10-10 of FIG. 9.

The inner wall surface of the stopper member receiving portion 31a, as shown in FIG. 10, is formed so as to define a generally rectangular space within the stopper member receiving portion 31a. Guide holes 37a and 37b are formed through both sides of stopper member receiving portion 31a. A ceiling portion of the stopper member receiving portion 31a includes a circular projection hole 37c. The upper side portion of the inner wall surface of the covering portion 31b defines a generally cylindrical space and the lower side portion of the covering portion 31b defines a generally rectangular space.

The needle tip protecting sleeve 32 includes a cylindrical body having an axial length which is slightly longer than the length of the protector body 31. The diameter of tip protecting sleeve 32 is smaller towards the rear end of sleeve 32 such that the rear end of the sleeve 32 defines a narrow opening 32a. The diameter of opening 32a is large enough to slidably receive the rear end of puncturing needle 21 but to small to allow passage of puncturing portion 21a of puncturing needle 21. The forward end of sleeve 32 defines a larger diameter opening 32b through which the puncturing portion 21a of puncturing needle 21 can be inserted. The outer diameter of the forward end of sleeve 32 is larger than the diameter of the rear end of engagement hole 35a. The outer diameter of the rear end of sleeve 32 is smaller than the diameter of the rear end of engagement hold 35a. Thus, sleeve 32 can be slid within engagement hole 35a from a retracted extending rearwardly from protector body 31 to an advanced positioned substantially located within protector body 31 but can not be removed from the rear end of engagement hole 35a because the outer diameter of the forward end of sleeve 32 can not pass through engagement hole 35a.

When the puncturing needle 21 is positioned within sleeve 32 and slid forwardly, the puncturing portion 21a of puncturing needle 21 projects or extends from the forward end of needle tip protecting sleeve 32. In that condition, the portion 21a of needle 21 is movable forwardly and backwardly from the rear portion of the protector body 31 through the insertion hole 36a and the engagement hole 35a. When the needle tip protecting sleeve 32 is accommodated in the protector body 31 in its advanced position, the needle tip protecting sleeve 32 passes through the insertion hole 36a to position the narrow opening portion 32a within the engagement hole 35a. When the needle tip protecting sleeve 32 is in its retracted position projecting from the rear portion of the protector body 31, the large diameter opening 32b of the needle protecting sleeve 32 engages the step of the engagement hole 35a, thereby preventing sleeve 32 from being pulled through engagement hole 35a.

The stopper member 33 is disposed within the protector body 31 so as to be upwardly and downwardly moveable. As shown in FIGS. 11 and 12, stopper member 33 includes a stopper body 33a and an engagement piece 33b. The stopper body 33a is disposed within the stopper member receiving portion 31a and the engagement piece 33b is positioned at a lower side portion of the covering portion 31b. The stopper body 33a is formed so as to be oblong and is provided with a frame body 38, having a square shaped stopper hole 38a formed in a center portion thereof. The stopper hole 38a extends through the body 38 and is dimensioned to receive sleeve 32. The upper and the lower surfaces defining the stopper hole 38a are convex such that the distance between the central portions thereof is shorter than at the ends. As such, the contact resistance caused by the passing the needle tip protecting sleeve 32 through hole 38 is decreased.

The upper portion of the body 38 includes, a cylindrical engagement portion 38b which is movable in relation to and into engagement with projection hole 37c of the protector body 31. Guide projections 38c and 38d are provided on opposite sides of body 38. Guide projections 38c and 38d are slidably positioned within guide holes 37a and 37b of the protector body 31 to guide movement of body 38. A lower portion of the stopper body 33a has a U shape cross section with the open side of the U shape facing downwardly. An engagement piece 33b extends forwardly from a lower end front portion of body 38. Further, an engagement claw 39 projects upwardly from a forward end of engagement piece 33b. Engagement claw 39 is positioned to engage projection 14d which is positioned on the outer periphery of housing tube 12b.

The stopper member 33, as described above, can be installed to the protector body 31 by positioning the guide projections 38c and 38d within the guide holes 37a and 37b, respectively. As discussed above, engagement between projections 38c and 38d and guide holes 37a and 37b, guide the up and down movement of stop member 33. The coil spring 34, which may be formed of stainless steel, is mounted about engagement portion 38b between the upper surface of the frame body 38 of the stopper member 33 and the ceiling portion of the stopper member receiving portion 31a of the protector body 31. The diameter of the coil spring 34 is larger than that of the projection hole 37c, thereby preventing it from projecting from the projection hole 37c.

Figure 13:
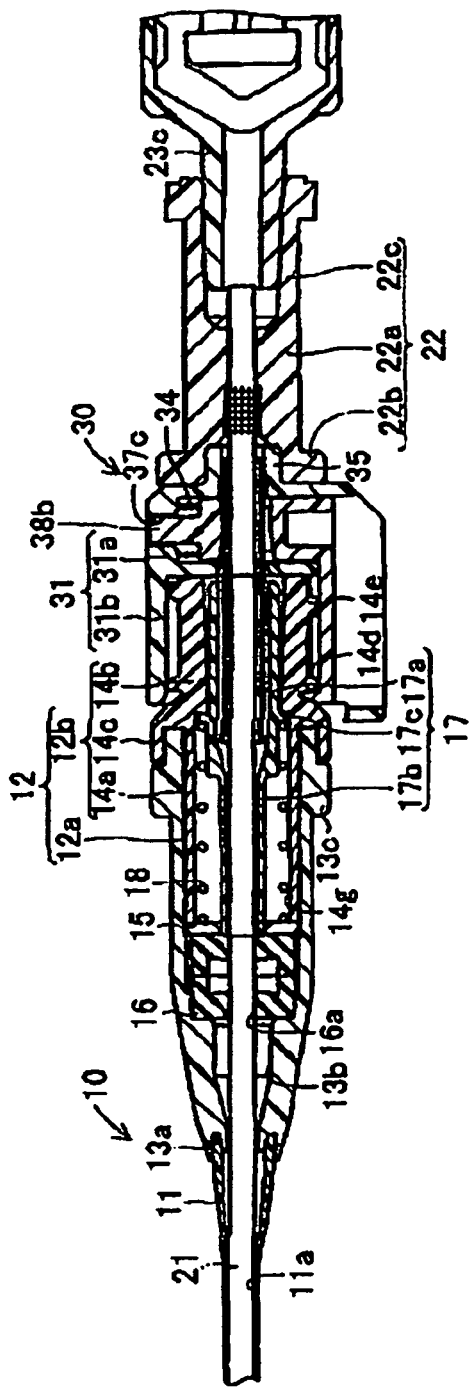
FIG. 13 is a cross sectional view illustrating the indwelling needle set shown in FIG. 1 with the needle tip protector device installed into the outer needle and with the inner needle positioned within the outer needle.

When the stopper member 33 is moved upwardly, the engagement portion 38b is positioned within the projection hole 37c as shown in FIG. 13 and the coil spring 34 is contracted or compressed by a force urging the stopper member 33 upwardly. When the force for urging the stopper member 33 upwardly is released, the coil spring 34 extends to move the stopper member 33 downwardly to the lower side of the protector body 31 as shown in FIG. 4. When the stopper member 33 is positioned in the lower side of protector body 31 and coil spring 34 is extended, guide projections 38c and 38d contact a lower end portion of guide holes 37a and 37b, respectively. In this position, the lower surface of the engagement piece 33b of the stopper member 33 is positioned at the lower end portion of the protector body 31.

The needle tip protector 30 is installed or secured to the housing 12 when the stopper member 33 is in the upper side of protector body 31 and coil spring 34 is compressed. During installation, tube portion 14b of housing tube 12b is positioned within the covering portion 31b of protector body 31 and needle tip protector 30, with the inner needle 20 disposed in the needle tip protecting sleeve 32, is inserted through the insertion hole 36a and the engagement hole 35a. When inner needle 20 is inserted through holes 35a and 36a, the stopper member 33 is maintained in the upper side of protector body 21 by the needle tip protecting sleeve 32 which is positioned within the stopper hole 38a of the frame body 38. In this position, the engagement portion 38b of stopper member 33 is positioned within the projecting hole 37c of protector body 31.

In the installed condition, the engagement claw 39 of the stopper member 33 is engaged with the projection 14d of the tube portion 14b to fix or secure needle tip protector 30 to the housing 12. When the inner needle 20 is pressed against the needle tip protecting sleeve 32, the engagement tube 35 of the protector body 31 is positioned within the receiving portion 22b of the hub 22 and the puncturing portion 21a of the puncturing needle 21 projects from the tip end portion 11b of the cannula 11.

When indwelling needle set A is in its installed condition, the coil spring 18 is extended such that the tube insertion portion 17 is positioned towards the rear end of the housing 12 and the forward end of the needle tip protecting sleeve 32 is positioned within the basal portion 17a of the tube insertion portion 17. The outer needle 10, the inner needle 20 and the needle tip protector 30 are installed in this way to provide the indwelling needle set A shown in FIGS. 1 to 3. In one embodiment, the cannula 11, the housing 12, the tube insertion portion 17, the protector body 31 and the stopper member 33 of the indwelling needle set A are formed from a resin material and the coil springs 18 and 34 and the needle tip protecting sleeve 32 are formed from a metallic material. Alternatively, other materials of construction are envisioned.

When using the indwelling needle set A, for example, to collect blood from the blood vessel of the patient, firstly, the tip end portion 11b of the cannula 11 together with the puncturing portion 21a of the puncturing needle 21 is inserted into the body of a patient to access a blood vessel. Then, the piston portion 23b of the syringe 23 is gradually pulled from or retracted within the cylinder part 23a of syringe 23. As this occurs, blood in the blood vessel is drawn into the puncturing needle 21 and enters the hub body 22a of the hub 22 and, therefore cylinder part 23a of syringe 23. As a result, blood can be visualized in cylinder port 23a of syringe 23 and/or hub 22 to confirm that puncturing needle 21 has entered a blood vessel.

Next, with the tip end portion 11b of the outer needle 10 positioned in the blood vessel of the patient, the inner needle 20 together with the syringe 23 is retracted toward the rear end of the outer needle 10. When this occurs, the puncturing needle 21 is retracted from within the outer needle 10. It is noted that as the inner needle 20 is withdrawn from the outer needle 10, the puncturing end 21a of inner needle slidably contacts the peripheral surface of the hole 16a of the valve 16. As the puncturing needle 21 passes through the hole 16a of the valve 16, the puncturing needle 21 and the inner peripheral surface of the hole 16a are in sealing contact with each other. Thus, blood is prevented from leaking out of the hole 16a. After the puncturing needle 21 is pulled from outer needle 10, the hole 16a of valve 16 will close to prevent blood from leaking to the rear end of the housing 12.

When the inner needle 20 is pulled toward the rear end of the outer needle 10, the puncturing portion 21a of the puncturing needle 21 engages the narrow opening portion 32a of the needle protecting sleeve 32 to effect rearward movement of the needle tip protecting sleeve 32. As the needle tip protecting sleeve 32 is moved rearwardly and the large diameter opening portion 32b of sleeve 32 passes through the inserting hole 36a of the diaphragm 36 and the stopper hole 38a of the stopper member 33, the stopper member 33 is urged downwardly to a lower side of protector body 31 by the restoration force of the coil spring 34. When this occurs, engagement claw 39 is moved downwardly and is disengaged from projection 14d of the tube portion 14b. Accordingly, the needle tip protector 30 is disengaged from the outer needle 10 and is separated from outer needle 10 with the puncturing needle 21 attached thereto to provide the condition shown in FIG. 4.

When needle tip protector 30 and puncturing needle 21 are separated from outer needle 10, the large diameter opening portion 32b of the needle tip protecting sleeve 32 is engaged with the step of the engagement hole 35a and the needle tip protecting sleeve 32 projects outwardly from the rear end of the protector body 31. In this position, the puncturing needle 21 cannot be pulled from the rear end of engagement tube 35 of protector body 31 because the puncturing portion 21a of the puncturing needle 21 is too large to pass through the narrow diameter opening portion 32a of the needle tip protecting sleeve 32. The puncturing needle 21 also cannot be advanced forwardly from protector body 31 because the stopper member 33 is positioned in front of the large diameter opening portion 32b of the needle tip protecting sleeve 32. Therefore, after use, access to puncturing portion 21a of needle 21 is prevented and the inner needle 20 and needle tip protector 30 can be disposed of in a safe manner.

Figure 14:
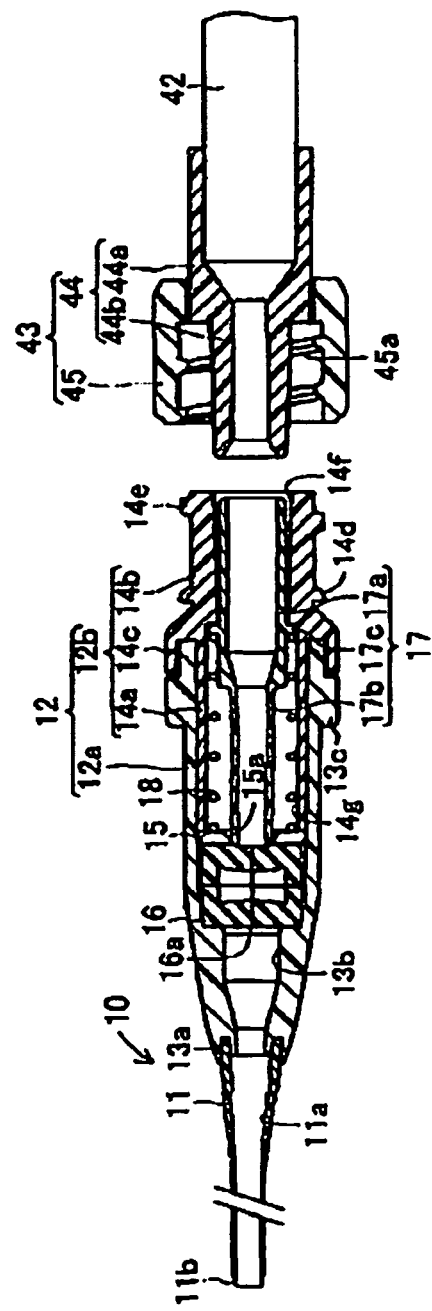
FIG. 14 is a cross sectional view of the outer needle assembly of the indwelling needle set after the needle tip protector device and the inner needle assembly have been removed positioned adjacent the connecting portion of a tube member.

Referring to FIGS. 4 and 14, after inner needle 20 and needle tip protector 30 have been separated from outer needle 10, the housing 12 of the outer needle 10 is connected to a tube member 42 (see FIG. 14) to supply a medicinal solution or the like to a patient. To accomplish this, a connecting portion 43 secured to the tip end of the tube member 42 is connected to the tube portion 14b of the housing 12 such that a forward end of the connecting portion 43 is received within the basal portion 17a of the tube insertion portion 17 as shown in FIG. 14. The connecting portion 43 includes a connecting portion body 44 which is fixed to the tip end portion of the tube member 42 and a cap like tube connecting portion 45 which is rotatably supported about the axis of the connecting portion body 44.

Figure 15:
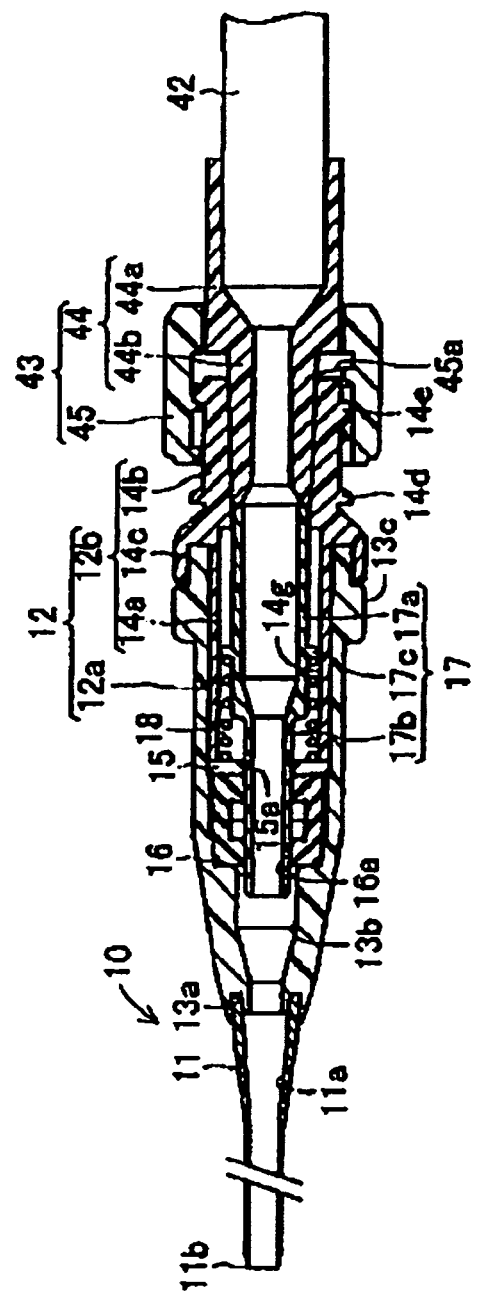
FIG. 15 is a cross sectional view of outer needle assembly of the indwelling needle set shown in FIG. 14 with the connecting portion of the tube member connected to the outer needle.

The connecting portion body 44 includes a fixing portion 44a which is fixed to the outer periphery of the tip end of the tube member 42, and a tapered male lure part 44b that can be inserted into the tube portion 14b to tightly contact an inner peripheral surface 14f of housing tube 12b. Connecting portion 45 has an internal thread 45a that is capable of being engaged with the external thread 14e of the housing 12. Engagement of internal thread 45a and external thread 14e draws the male lure part 44b into the tube portion 14b to connect the outer needle 10 to tube member 42 as shown in FIG. 15.

When the connecting portion 43 is connected to the outer needle 10, the male lure part 44b engages the rear end of the tube insertion portion 17 to move tube insertion portion 17 forwardly against the elasticity of the coil spring 18. As tube insertion portion 17 moves forwardly, the insertion end 17b of the tip end side of the tube insertion portion 17 penetrates the hole 16a of the valve 16. When insertion end 17b of tube insertion portion 17 penetrates hole 16a of valve 16, a lumen defined by tube insertion portion 17 fluidly communicates with the lumen 11a of the cannula 11 through the space 13b of the housing body 12a. Accordingly, a feeder (not shown), e.g., an IV bottle, for medicinal solution or the like which is connected to the basal end portion of the tube member 42 can supply fluid to cannula 11 when the connecting portion 43 is secured to the outer needle 10 to supply fluid to a blood vessel.

As discussed above, the needle tip protector 30 in accordance with this embodiment of the disclosure includes the protector body 31 and the needle tip protecting sleeve 32. The needle tip protecting sleeve 32 is movable forwardly and backwardly between an advanced position located inside of the protector body 31 and a retracted position in which the sleeve 32 projects rearwardly through the engagement hole 35a of the engagement tube 35 of the protector body 31. Further, the forward puncturing portion 21a of the puncturing needle 21 is formed so as to have a greater diameter than the rear portion of the puncturing needle 21 such that the rear portion of the puncturing needle 21 can be inserted through the needle tip protecting sleeve 32, but the forward puncturing portion 21a of the needle 21 cannot pass through the narrow diameter opening portion 32a of protective sleeve 32.

In summary, the tip end portion 11b of the cannula 11 and the puncturing portion 21a of the puncturing needle 21 of the indwelling needle set A, are inserted into the body of the patient. Thereafter, the outer needle 10 is retracted in relation to the inner needle 20 to separate the inner needle 20 from the outer needle 10. The inner needle 20 is withdrawn through engagement hole 35a of tip protector 30 such that the puncturing portion 21a of needle 21 engages the narrow diameter opening 32a of the needle tip protecting sleeve 32. When this occurs, the needle tip protecting sleeve 32, while it covers the puncturing portion 21a, is withdrawn through hole 35a of the protector body 31. When the needle tip protecting sleeve 32 is withdrawn through the stopper hole 38a of the stopper member 33, the needle tip protecting sleeve 32 is disengaged from the stopper member 33. Therefore, the stopper member 33 is moved by the coil spring 34 to the position where it covers the engagement hole 35a.

Because, as discussed above, the puncturing portion 21a of the puncturing needle 21 can not be retracted from the narrow diameter opening portion 32a or advanced into the protector body 31, the puncturing portion 21a of needle 21 can be maintained in a safe condition where it is covered by the needle tip protector 30. Therefore, inner needle assembly 20 and needle tip protector 30 can be safely discarded. Moreover, when the needle tip protector 30 is installed onto the indwelling needle set A, the needle tip protecting sleeve 32 is positioned within the protector body 31. Thus, the length of the indwelling needle set A has not been increased by the length of such a sleeve. Accordingly, the operativity of the indwelling needle set A need not be decreased.

The projection 14d is provided on the housing 12 and the engagement piece 33b including the engagement claw 39 is provided on the stopper member 33. The engagement claw 39 is engaged with the projection 14d when the needle tip protecting sleeve 32 is positioned within the stopper hole 38a of the stopper member 33. In turn, the engagement of the engagement claw 39 with the projection 14d is released when the needle tip protecting sleeve 32 is withdrawn from the stopper hole 38a. When the inner needle 20 is withdrawn from the outer needle 10, the needle tip protecting sleeve 32 mounts to the puncturing portion 21a of the puncturing needle 21 and separation of sleeve 32 and needle 21 is prevented. Further, the needle tip protector 30 can be detached from the outer needle 10 together with the inner needle 20. Therefore, the attachment of the needle tip protecting sleeve 32 to the puncturing portion 21a and the detachment of the needle tip protector 30 from the outer needle 10 can be performed only by the operation of withdrawing the inner needle 20 from the outer needle 10.

The needle tip protector in accordance with the disclosure is not intended to be limited to the embodiments described above, i.e., various modifications can be made thereto by those of ordinary skill in the art. For example, in the above described embodiment, though the indwelling needle set including the needle tip protector is inserted into a blood vessel, the indwelling needle set including the needle tip protector in accordance with the present disclosure may be applied not only to blood vessels but also to sites in the body such as the intestine, for example, duodenum; pyelitis; or urinary bladder.

Although the protector sleeve is described as having a stepped portion and a narrow diameter portion for engaging the puncturing portion of the needle, other configurations may be provided so long as the engagement portion and the engagement opening portion can be engaged with each other. For example, a needle having a constant outer diameter and a projection formed at the tip end portion of the needle may be provided in combination with a sleeve having a portion capable of being engaged with that projection. In this case, the projection included in the puncturing needle may be in the form a ring like projection along the circumference of the needle, a projection formed at one position on the circumference of the needle, or a plurality of projections formed at a plurality of positions about the circumference of the needle.

Alternatively, a needle having a constant outer diameter and a recess provided at the tip end portion can be provided as the puncturing needle for use in association with a portion on the sleeve capable of being engaged with the recess. According to this embodiment, the puncturing needle can be engaged with the needle tip protecting sleeve when the projections and the like are engaged with the recess. Further, the recess included in the puncturing needle in this case may be in any form such as a ring like recess along the circumference of the needle, a recess formed at one position on the circumference of the needle, or a plurality of recesses formed at a plurality of positions on the needle.

What is claimed is:

1. A needle tip protection device comprising:
a needle tip protector body having a front portion configured to receive a basal end of an outer needle and a rear portion defining a rearwardly extending engagement tube defining a hole;
a stopper member supported by the rear portion of the needle tip protector body, the stopper member being movable from a first position, in which the member obstructs the hole of the engagement tube, to a second position, in which the member provides access to the hole of the engagement tube;
a protecting sleeve slidably positioned within the hole of the engagement tube and movable between a first advanced position, in which the sleeve extends through the hole in the engagement tube and past the stopper member, and a retracted position, in which the sleeve extends rearwardly from the needle tip protector body through the hole of the engagement tube, the protecting sleeve having a forward end and a rear end, the rear end of the protecting sleeve being dimensioned to be slidably received in the hole of the engagement tube and the forward end of the protecting sleeve being dimensioned to prevent passage of the forward end of the protecting sleeve through the hole of the engagement tube so the protecting sleeve remains connected to the protector body, the protecting sleeve defining a bore having a forward opening having a first diameter and a rear opening having a second diameter smaller than the first diameter; and
an inner needle having a needle tip smaller than the first diameter and larger than the second diameter.

2. The needle tip protection device according to claim 1, wherein the stopper member defines a hole, the hole in the stopper member being aligned with the hole in the engagement tube when the stopper member is in its second position and misaligned with the hole in the engagement tube when the stopper member is in its first position, the hole in the stopper member being dimensioned to permit passage of the protector sleeve.

3. The needle tip protection device according to claim 2, wherein the stopper member is urged to its first position by a spring.

4. The needle tip protection device according to claim 3, wherein the protecting sleeve extends through the hole in the stopper member when the protecting sleeve is in the advanced position, the protecting sleeve engaging walls of the sleeve defining the hole in the stopper member to retain the stopper member in its second position.

5. The needle tip protection device according to claim 4, wherein the walls of the sleeve defining the hole in the stopper member are convex.

6. The needle tip protection device according to claim 2, wherein the needle tip protector body further includes a diaphragm separating the front portion of the needle tip protector body and the rear portion of the needle tip protector body, the diaphragm defining an insertion hole which is aligned with the hole in the engagement tube.

7. The needle tip protection device according to claim 1, wherein the stopper member includes an engagement piece configured to secure the needle tip protector body to a needle housing of an indwelling needle set when the stopper member is in the second position.

8. The needle tip protection device according to claim 7, wherein the engagement piece of the stopper member includes an engagement claw.

9. The needle tip protection device according to claim 1, wherein the hole in the engagement tube defines a stepped bore, a rear portion of the stepped bore having a diameter which is smaller than a diameter of a forward portion of the stepped bore.

10. The needle tip protection device according to claim 9, wherein a step is defined between the forward portion of the stepped bore and the rear portion of the stepped bore, the forward end of the protecting sleeve engaging the step when the protecting sleeve is in its retracted position.

11. An indwelling needle set comprising:
an outer needle including a cannula and a housing body defining a chamber;
an elastic valve supported within the chamber;
an inner needle having a forward puncturing end and a rear end, the forward puncturing end having an enlarged diameter portion; and
a needle tip protection device including:
  i) a needle tip protector body having a front portion configured to receive the rear end of the housing of the outer needle and a rear portion defining a rearwardly extending engagement tube defining a hole;
  ii) a stopper member supported within the rear portion of the needle tip protector body, the stopper member being movable from a first position obstructing the hole of the engagement tube to a second position providing access to the hole of the engagement tube; and
  iii) a protecting sleeve slidably positioned within the hole of the engagement tube and movable between a first advanced position, in which the sleeve is located within the needle tip protector body, and a retracted position, in which the sleeve extends rearwardly from the needle tip protector body through the hole of the engagement tube, the protecting sleeve having a forward end and a rear end, the rear end of the protecting sleeve being dimensioned to be slidably received in the hole of the engagement tube and the forward end of the protecting sleeve being dimensioned to prevent passage of the forward end of the protecting sleeve through the hole of the engagement tube so the protecting sleeve remains connected to the protector body, wherein the protecting sleeve defines a bore having a forward opening having a first diameter and a rear opening having a second diameter smaller than the first diameter, the inner needle being slidably positioned within the protecting sleeve, the enlarged diameter portion of the inner needle being greater in diameter than the second diameter of the rear opening of the protecting sleeve so the inner needle cannot be withdrawn from the protecting sleeve.

12. The indwelling needle set according to claim 11, further including a tub insertion portion movably supported within the housing, the tube insertion portion defining a bore and being movable from a rearward position to a forward position, an insertion end of the tube insertion portion extending through an opening in the elastic valve.

13. The indwelling needle set according to claim 12, wherein the tube insertion portion is urged towards its rearward position by a spring.

14. The indwelling needle set according to claim 11, wherein the housing body includes an external thread adapted to engage a tube member for supplying medicinal fluid to the needle set.

15. The indwelling needle set according to claim 11, wherein the inner needle includes a hub member supported on a rear end of the inner needle.

16. The indwelling needle set according to claim 11, wherein the stopper member defines a hole, the hole in the stopper member being aligned with the hole in the engagement tube when the stopper member is in its second position and misaligned with the hole in the engagement tube when the stopper member is in its first position, the hole in the stopper member being dimensioned to permit passage of the protector sleeve.

17. The indwelling needle set according to claim 16, wherein the stopper member is urged to its first position by a coil spring.

18. The indwelling needle set according to claim 17, wherein the protecting sleeve extends through the hole in the stopper member when the protecting sleeve is in the advanced position, the protecting sleeve engaging walls of the sleeve defining the hole in the stopper member to retain the stopper member in its second position.

19. The indwelling needle set according to claim 18, wherein the walls of the sleeve defining the hole in the stopper member are convex.

20. The indwelling needle set according to claim 16, wherein the needle tip protector body further includes a diaphragm separating the front portion of the needle tip protector body and the rear portion of the needle tip protector body, the diaphragm defining an insertion hole which is aligned with the hole in the engagement tube.

21. The indwelling needle set according to claim 11, wherein the stopper member includes an engagement piece configured to secure the needle tip protector body to the housing body of the outer needle when the stopper member is in the second position.

22. The indwelling needle set according to claim 21, wherein the engagement piece of the stopper member includes an engagement claw and the housing body of the outer needle includes a projection, the engagement claw being positioned to engage the projection when the stopper member is in its second position to secure the needle tip protector body to the housing body and to disengage the projection when the stopper member is in its first position to detach the needle tip protector body from the housing body.

23. The indwelling needle set according to claim 11, wherein the hole in the engagement tube defines a stepped bore, a rear portion of the stepped bore having a diameter which is smaller than a diameter of a forward portion of the stepped bore.

24. The indwelling needle set according to claim 23, wherein a step is defined between the forward portion of the stepped bore and the rear portion of the stepped bore, the forward end of the protecting sleeve engaging the step when the protecting sleeve is in its retracted position.

\* \* \* \* \*